United States Patent
Chen et al.

(10) Patent No.: US 11,026,381 B2
(45) Date of Patent: Jun. 8, 2021

(54) METHOD FOR PRODUCING HAPLOID, DIHAPLOID AND DOUBLED HAPLOID PLANTS BY ISOLATED MICROSPORE CULTURE

(71) Applicant: Vilmorin & Cie, Paris (FR)

(72) Inventors: Jianxin Chen, Davis, CA (US); Elise Vanek, Davis, CA (US); Mark Pieper, Davis, CA (US)

(73) Assignee: Vilmorin & Cie, Paris (FR)

(*) Notice: Subject to any disclaimer, the term of this patent is extended or adjusted under 35 U.S.C. 154(b) by 428 days.

(21) Appl. No.: 15/747,631

(22) PCT Filed: Jul. 26, 2016

(86) PCT No.: PCT/EP2016/067825
§ 371 (c)(1),
(2) Date: Jan. 25, 2018

(87) PCT Pub. No.: WO2017/017108
PCT Pub. Date: Feb. 2, 2017

(65) Prior Publication Data
US 2018/0213736 A1    Aug. 2, 2018

(30) Foreign Application Priority Data
Jul. 28, 2015 (EP) .................................... 15306231

(51) Int. Cl.
*A01H 6/34* (2018.01)
*A01H 1/08* (2006.01)
*A01H 1/04* (2006.01)
*A01H 3/04* (2006.01)
*A01H 4/00* (2006.01)

(52) U.S. Cl.
CPC .............. *A01H 1/08* (2013.01); *A01H 1/04* (2013.01); *A01H 3/04* (2013.01); *A01H 4/005* (2013.01); *A01H 4/008* (2013.01); *A01H 6/34* (2018.05)

(58) Field of Classification Search
None
See application file for complete search history.

(56) References Cited

U.S. PATENT DOCUMENTS

| 6,511,990 B1 | 1/2003 | Breslow |
| 2011/0237832 A1 | 9/2011 | Helquist et al. |
| 2016/0212956 A1* | 7/2016 | Boutilier .................. A01H 1/08 |

FOREIGN PATENT DOCUMENTS

| CN | 101317548 A | 12/2008 |
| EP | 0374755 A1 | 6/1990 |
| WO | WO 97/11366 A1 | 3/1997 |
| WO | WO 98/48825 A1 | 4/1998 |
| WO | WO 00/08048 A2 | 2/2000 |
| WO | WO 2015/043621 A1 | 4/2015 |

OTHER PUBLICATIONS

Kumar et al. (European Journal of Horticultural Science 69 (2004): 201-205). (Year: 2004).*
Gałązka et al. (Folia Horticulturae 25.1 (2013): 67-78). (Year: 2013).*
Cha-um et al. (In Vitro Cellular & Developmental Biology-Plant 45.2 (2009): 171-179). (Year: 2009).*
K. Andrews et al., "Anti-malarial effect of histone deacetylation inhibitors and mammalian tumour cytodifferentiating agents", International Journal for Parasitology; 2000; vol. 30, pp. 761-768.
H.G. Ashok Kumar et al., "Embryogenesis and plant regeneration from anther cultures of *Cucumis sativus* L." Scientia Horiculturae; 2003; vol. 98, pp. 213-222.
H.G. Ashok Kumar & H.N. Murthy, "Effect of sugars and amino acids on adrogenesis of *Cucumis sativus*"; Plant Cell, Tissue and Organ Culture; 2004; vol. 78, pp. 201-208.
Gerald Brosch, et al., "Inhibition of Maize Histone Deacetylases by HC Toxin, the Host-Selective Toxin of *Cochliabolus carbonum*", The Plant Cell; Nov. 1995; vol. 7, pp. 1941-1950.
Lawrence S. Cousens, et al., "Different Accessibilities in Chromatin to Histone Acetylase", The Journal of Biological Chemistry; Mar. 10, 1979; vol. 254, No. 5, pp. 1716-1723.
Sandra J. Darkin-Rattray, et al., "Apicidin: A novel antiprotozoal agent that inhibits parasite histone deacetylase".
A.M. De Laat & J. Blaas, "Flow-cytometric characterization and sorting of plant chromosomes", Theor Appl Genet; 1984; vol. 67, pp. 463-467.
De Laat, et al., "Determination of Ploidy of Single Plants and Plant Populations by Flow Cytometry", Plant Breeding; 1987; vol. 99, pp. 303-307.
Robin R. Frey, et al., "Trifluoromethyl Ketones as Inhibitors of Histone Deacetylase", Bioorganic & Medicinal Chemistry Letters; 2002; vol. 12, pp. 3443-3447.
Rong J. Guan, et al., "Drg-1 as a Differentiation-related, Putative Metastatic Suppressor Gene in Human Colon Cancer", Cancer Research; Feb. 1, 2000; vol. 60, pp. 749-755.

(Continued)

*Primary Examiner* — Charles Logsdon
(74) *Attorney, Agent, or Firm* — John P. White

(57) ABSTRACT

The present invention relates to a method for producing haploid, dihaploid, polyhaploid and/or doubled haploid plants of the family Cucurbitaceae from isolated microspores, wherein said method comprises a) culturing isolated microspores to obtain embryos competent for plant regeneration, wherein the microspores have been isolated from plant material of a donor plant of the family Cucurbitaceae; and b) regenerating plants from the embryos; wherein step (a) comprises contacting the microspores with one or more inhibitor of histone deacetylase (HDACi) and one or more polyamine. The present invention also relates to a method for producing haploid, dihaploid, polyhaploid and/or doubled haploid embryos, to related kits and compositions, and to plants obtained according to the methods.

16 Claims, 4 Drawing Sheets

(56) References Cited

OTHER PUBLICATIONS

Harvey & Kielkowska, "Studies on in vitro culture of cucumber microspores" Plant and Animal Genome Conference; 2010; Paper No. P871, abstract.

D. Hosemans & D. Bossoutrot, "Induction of Haploid Plants from in vitro Culture of Unpollinated Beet Ovules (*Beta vulgaris* L.)", Z. Planzenzüchtg.; 1983; vol. 91, pp. 74-77.

W.A. Keller, et al., The Production and Utilization of Microspore-Derived Haploids in *Brassica* Crops; Plant Cell Culture in Crop Improvement, Basic Life Sciences; 1983; vol. 22, pp. 169-183, abstract.

Ho Jeong Kwon, et al., "Depudecin induces morphological reversion of transformed fibroblasts via the inhibition of histone deacetylase", Proc. Natl. Acad. Sci.; Mar. 1998; vol. 95, pp. 3356-3361.

J.E. Lazarte & C.C. Sasser, "Asexual Embryogenesis and Plantlet Development in Anther Culture of *Cucumis sativus* L.", HortScience; 1982; vol. 17(1):88.

Michael A. Lea & Nirman Tulsyan; "Discordant Effects of Butyrate Analogues on Erythroleukemia Cell Proliferation, Differentiation and Histone Deacetylase" Anticancer Research; 1995; vol. 15, pp. 879-884.

John A. McBain, et al., "Apoptotic Death in Adenocarcinoma Cell Lines Induced by Butyrate and other Histone Deacetylase Inhibitors", Biochemical Pharmacology; 1997; vol. 53, pp. 1357-1368.

Akiko Saito, et al., "A synthetic inhibitor of histone deacetylase, MS-27- 275, with marked in vivo antitumor activity against human tumors", Proc. Natl. Acad. Sci.; 1999; vol. 96, pp. 4592-4597.

K.R. Sarkar & E.H. Coe, Jr, "A Genetic Analysis of the Origin of Maternal Haploids in Maize"; Aug. 1966; vol. 54, pp. 453-464.

Annie Sauton & R.D. De Vaulx, "Obtention de plantes haploïdes chez le melon (*Cucumis melo* L.) par gynogenèse induite par du pollen irradié", Agronomie; 1987; vol. 36, No. 2, pp. 141-148, including English language.

Sipra Guha & S.C. Maheshwari, "In vitro Production of Embryos from Anthers of *Datura*", Nature; Oct. 31, 1964; vol. 204, p. 497.

Gloria H. Su, et al., "A Novel Histone Deacetylase Inhibitor Identified by High-Throughput Transcriptional Screening of a Compound Library" Cancer Research; 2000; vol. 60, pp. 3443-3447.

Jianxiang Wang, et al., "Inhibitors of Histone Deacetylase Relieve ETO-mediated Repression and Induce Differentiation of AML1-ETO Leukemia Cells", Cancer Research; 1999; vol. 59, pp. 2766-2799.

Zhan Yan, et al., "Embryoid Induction and Plant Regeneration of Cucumber (*Curcumis sativus* L.) Through Microspore Culture", Acta Horticulturae Sinica; 2009; vol. 36, No. 2, pp. 221-226, including English language.

LI, H., et al., "The Histone Deacetylase Inhibitor Trichostatin A Promotes Totipotency in the Male Gametophyte", The Plant Cell, American Society of Plant Biologists, U.S., vol. 26, No. 1, Jan. 1, 2014, pp 195-209.

Joanna Galazka, et al., "Review of research on haploid production in cucumber and other cucurbits", Folia Horticulturae, vol. 25, No. 1, Jan. 1, 2013, pp. 72-73.

H.G. Ashok Kumar, et al., "The Influence of Polyamines on Androgenesis of *Cucumis sativus* L", Verlag, Eugen Ulmer GmbH & Co. Stuttgart, Europ. J. Hort. Sci., Jan. 1, 2004, pp. 201-205.

Hui Song, et al. "Regeneration of doubled haploid plants by androgenesis of cucumber (*Cucumis sativus* L.)", Plant Cell, Tissue and Organ Culture, Cluwer. Academic Publishers, DO, vol. 90, No. 3, Jul. 19, 2007, pp. 245-254.

International Search Report dated Oct. 14, 2016 in connection with PCT International Application No. PCT/EP2016/067825.

Written Opinion of the International Searching Authority dated Oct. 14, 2016 in connection with PCT International Application No. PCT/EP2016/067825.

\* cited by examiner

A.

B.

A.

B.

C.

METHOD FOR PRODUCING HAPLOID, DIHAPLOID AND DOUBLED HAPLOID PLANTS BY ISOLATED MICROSPORE CULTURE

CROSS-REFERENCE TO RELATED APPLICATIONS

This application is a § 371 national stage of PCT International Application No. PCT/EP2016/067825, filed Jul. 26, 2016, claiming priority of European Patent Application No. EP 15306231.0, filed Jul. 28, 2015, the contents of each of which are hereby incorporated by reference into the application.

The present invention relates to the field of plant selection or improvement, namely the production of plants both in the form of embryos and at any other stage, notably from the plantlet to the adult plant.

In particular, plant selection or improvement according to the present invention aims at obtaining a homozygous or essentially homozygous haploid or diploid plant having progeny that is stable in terms of its phenotypic and/or genotypic characters. In other words, the method of the invention can lead to fixation of the genome of a plant with a reduced number of generations (for example one or two).

More particularly, the present invention relates to a novel method for producing plants (e.g. embryos, plantlets, adult plants) that are haploid, doubled haploid, dihaploid and/or polyhaploid, homozygous or essentially homozygous, this method being a method such as those which come under the technique of Isolated Microspore Culture. The plants in question are cucurbits plants such as cucumber (*Cucumis sativus*), melon (*Cucumis melo*), watermelon (*Citrullus lanatus*) or squash (*Cucurbita pepo*) plants.

The systems for, creating varieties, namely the creation of novel plants to meet the specific needs of farmers and producers, have accelerated since the beginning of the $20^{th}$ century. One of the most radical changes was the development of hybrids, also called F1 hybrids commercially, initially in maize, and utilization of the phenomenon of heterosis, which corresponds to increase in the capacities or vigor of a hybrid for a number of characters (vigor, yield, resistance to diseases and lodging resistance, precocity, etc.) above the average of the two parents or above the best of the two parents. Another change relates to the use of in vitro plant culture techniques based on their totipotency.

The creation of F1 hybrid plants, notably making it possible to combine, in the F1 hybrid plant, the dominant characters of its parents, was quickly extended from maize to other species such as tomato, peppers, eggplants. In fact, in addition to the hybrid vigor present in certain species, obtaining F1 hybrids also makes it possible to improve the plant's capacities for homeostasis (stability of the plant and of expression of its characters in different environments), and the possibility of cumulating genes of interest. However, the creation of F1 hybrid plants involves the provision of relatively homozygous parental lines. Once crossed, these parental lines make it possible to obtain reproducibly the F1 hybrid. As long as the genetic purity of the parental lines is maintained, the F1 hybrids can be obtained repeatedly.

This quest for homozygosity of the parental lines was not developed solely for obtaining F1 hybrid plants. Similarly, during development of new plants marketed in the form of population varieties (lettuce, bean, corn, salad, etc.), the creation of relatively homozygous cultivars (or varieties) has become imperative. The requirements of product homogeneity for farmers and for marketing (criteria of homogeneity and stability of new cultivars included in the list), as well as mechanization and the increasing precision of techniques for culture and production, lead to the need for plants that are more and more homogeneous in expression of their characters.

The plant breeder traditionally gets closer to the level of required homozygosity by self-fertilizing the most promising plants over several generations, selecting those that have the required characters, thus progressively homogenizing the genome of the plants from one generation to the next.

The new plants developed by plant breeders are either autogamous cultivars, or F1 hybrids. In both cases, achieving homogeneity of the cultivar and/or of the parental lines of the F1 hybrid is one of the goals of the selection program.

It will be recalled that to initiate the sexual cycle of plants, a process of reduction of the number of chromosomes (meiosis) is necessary to give rise to gametes having a haploid chromosome number (n). In flowering plants, sexual reproduction involves double fertilization. The pollen grain produces two male gamete nuclei (n) or reproductive nuclei. A male nucleus fuses with an ovule (n) to form a zygote (2n) which produces the embryo by restoring the number of somatic chromosomes (2n). Another male nucleus (n) combines with the haploid polar nuclei of the embryo sac, to form a triploid cell (3n). In certain cases, formation of the zygote does not occur, but cell divisions of the ovule are nevertheless initiated, resulting in a haploid embryo capable of giving rise to a plantlet whose haploid genome originates entirely from the female plant (Sarkar and Coe, Genetics, 1966, Vol. 54, 453-464). Haploid plants occur in small numbers in nature and are sterile.

The discovery, at the beginning of the 1920s, of viable haploid plants and of the possibility of doubling their chromosome stock was the stimulus for much research. In fact, these haploid plants are interesting not only in the field of genetics but also for plant improvement because, after chromosome doubling (whether or not spontaneous), the genetic information is identical on the two chromosomes of each pair. Accordingly, the genetic information is fixed and the doubled haploids can speed up the selection processes.

In 1964, Guha and Maheshwari (Guha and Maheshwari, Nature, 1964, Vol. 204, pp. 497) discovered that plants can be regenerated from haploid cells during culture of pollen grains.

Since then, numerous studies have investigated the production of haploid plants of various species, using techniques of in vitro culture of gametophytes. The two main techniques for production of embryos and haploid plants (haploidization) by in vitro culture of gametophytes are androgenesis and gynogenesis: In gynogenesis, mature female gametophytes (ovaries or ovules) are cultured on a synthetic medium in order to obtain haploid embryos, which then develop into complete plants. In androgenesis, it is the immature male gametophytes that are cultured. In both techniques, the results vary with the protocols used but even more these techniques are known and recognized as being dependent on the genotype, meaning that one protocol will work for one variety but not for another one.

Some authors also mention the production of embryos and of haploid plants by the use of chemical or physical agents. The principle of this technique is to bring about the development of the unfertilized ovule on the plant (in situ). Although trials with thermal shock, X-rays or chemicals only gave mediocre results, the use of irradiated pollen gave, in certain species such as the melon, results that are however not directly applicable to other species.

The majority of the plants induced by these techniques are haploid plants, but other plants with variable levels of ploidy can be obtained. Although aneuploids or tetraploids may only be of minor interest in plant improvement programs, spontaneous diploids (dihaploids DiH) are for their part very sought-after, since the spontaneous doubling of their chromosome stock during the first phases of culture in vitro renders them fertile. These homozygous plants can be used directly by plant breeders, which represents an enormous advantage on several levels (time, space, cost, etc.).

The haploid plants that are obtained by these various techniques and that have not spontaneously doubled their chromosome stock must then undergo an additional stage to render them diploid (2n), namely doubled haploids. This can be done by means of various chemicals such as colchicine (an alkaloid that permits doubling of a chromosome stock).

The doubled haploids as well as the dihaploids (resulting from spontaneous diploidization) are homozygous individuals, which can be used notably directly as homogeneous cultivars (population varieties) or as parental lines of hybrid varieties. In fact, these doubled haploid and dihaploid plants carry, in doubled form, the genetic information of a single set (n) of chromosomes, that of the gamete from which they were originally derived.

Thus, these techniques for creation of plants in vitro not only save time, but also lead to better genetic homogeneity: the genome is stabilized (homozygous) in a single generation instead of approaching genomic homozygosity after multiple generations of self-fertilization. They also make it possible to improve the selection program since they emphasize the recessive characteristics of the plant thus created. The use of doubled haploids DH and dihaploids DiH is therefore a very interesting tool. Its use has been widely adopted for certain species: androgenesis is used for plants of the genus Brassica (Keller et al., in K. Giles, S. Sen (eds.), Plant Cell Culture in Crop Improvement, 1984, 169-183. Plenum Pub. Corp., New York), gynogenesis for cucumber (European patent EP 0374755) and sugar beet (Hosemans and Bossoutrot, Z. Pflanzenzuecht, 1983, 91, 74-77), irradiated pollen for melon (Sauton and Dumas de Vaulx, Agronomie 7, 1987, 7 (2), 141-148).

However, despite a few commercial varieties, the yields of the various methods of haploidization are still too dependent on multiple factors that are unknown or imperfectly controlled such as genotype, culture of the mother plants, conditions in which haploidization is performed, etc. and are sometimes still too low, in many species, to be integrated routinely in the existing methods of selection.

There is therefore a need for a more reliable, repeatable and efficient system to produce cucurbit plants such as cucumber plants. Today, there are few reports about the production of cucumber haploid, dihaploid and doubled haploid embryos from male gametophytes: *Cucumis sativus* anther culture was reported in 1982 by Lazarte and Saaser in 1982 (*HortScience* 17:88), but without the regeneration of plants from the culture.

Then, Kumar et al, in 2003 (*Scientia Hoticulturae* 98: 213-222) described the response of cucumber anther to in vitro culture on two cultivars, and found that such culture is genotype dependent as, both cultivar used did not follow the same pattern for embryogenesis (direct or through callus development). The same team, in 2004 (*Plant Cell Tiss. Organ Cult.* 78: 201-208 & *Europ. J. Hort. Sci.* 69(5) 201-2015) reported the effect of sugars, amino acids and polyamines in anther culture. Both the genotype dependence and the low anther culture efficiency limit the applications of these methods in breeding.

In 2007, Song et al. in Regeneration of doubled haploid plants by androgenesis of cucumber (*Plant Cell Tiss. Organ Cult.* 90: 245-254) developed another anther culture protocol, that was slightly more efficient but in any cases still genotype dependent.

Further, embryogenesis derived from *Cucumis sativus* anther cultures is quite often derived from somatic tissues of the anther, such as the anther wall and/or the filament. The plants thus obtained are diploid plants but heterozygous as they did not undergo the gametic reduction during the formation of the male gametes.

Another method of androgenesis uses isolated microspores rather than anthers.

The only known cultivation method for isolated microspores of *Cucumis sativus* plants (cucumber) has been disclosed in Chinese patent application 200810022098.5 as well as in Zhan et al., *Acta. Horticulturae Sinica*, 2009, 36 (2), 221-226. The authors have cultured isolated microspores from 10 different varieties of cucumber and cotyledonary embryoids and plantlets have been allegedly obtained for two varieties out of 10.

This protocol is thus once again highly genotype dependent, as evidenced by the low rate of success amongst different genotypes. Moreover, the inventors of the present invention have followed the described protocol with genotypes claimed as leading to embryos and plantlets, but they failed to reproduce the teaching of neither the scientific publication nor the patent and did not obtain any embryo or plantlets (see Example 1).

As of today, there is therefore still a lack of an efficient method for producing haploid, dihaploid, polyhaploid and/or doubled haploid cucurbitacea plants, especially *Cucumis sativus* plants by isolated microspore cultures. Further, there is a need to provide such a method in a non-genotype dependent way.

In this context, one of the aims of the present invention is to provide a method for improving the production of haploid, dihaploid, polyhaploid and/or doubled haploid haploid cucurbitacea plants, especially *Cucumis sativus* plants by isolated microspore cultures, especially in a non-genotype dependent way.

Another aim of the invention is to provide embryos, plantlets and plants regenerated from the embryo, progeny of such plants and seed from such plants, usable in or obtained by or obtainable by a method for improving the production of haploid, dihaploid, polyhaploid and/or doubled haploid cucurbitacea plants, especially *Cucumis sativus* plants by isolated microspore cultures, especially in a non-genotype dependent way.

Such aims are achieved by the present invention which relates, in one aspect, to a method for producing embryos and/or plants of the family Cucurbitaceae from isolated microspores, wherein said method comprises:

a) culturing isolated microspores to obtain embryos competent for plant regeneration, wherein the microspores have been isolated from plant material of a donor plant of the family Cucurbitaceae; and b) optionally regenerating plants from the embryos;

wherein step (a) comprises contacting the microspores with one or more inhibitor of histone deacetylase (HDACi) and one or more polyamine.

The method for producing cucurbitacea embryos and/or plants according to the present invention is surprising not only because it applies in a non-genotype dependent way while all previously known literatures and protocols always mentions such genotype dependence, but also because it could be applied to different cucurbitacea plants. While originally designed in for the production of haploid, dihaploid, polyhaploid and/or doubled haploid *Cucumis sativus* embryos, plantlets and plants, the method can also be applied to other cucurbitacea plants such as *Cucumis melo, Cucurbita pepo* and/or *Citrullus lanatus*.

In one embodiment, the plants and/or embryos produced according to the present invention comprise or consist of haploid, dihaploid, polyhaploid, doubled haploid, aneuploid and/or alleuploid plants. In another embodiment, the plants and/or embryos produced according to the present invention comprise or consist of haploid, dihaploid, polyhaploid and/or doubled haploid plants. In another embodiment, the plants and/or embryos produced according to the present invention comprise or consist of dihaploid, polyhaploid and/or doubled haploid plants. In another embodiment, the plants and/or embryos produced according to the present invention comprise or consist of dihaploid and polyhaploid plants. In another embodiment, the plants and/or embryos produced according to the present invention comprise or consist of dihaploid and doubled haploid plants. In another embodiment, the plants and/or embryos produced according to the present invention comprise or consist of dihaploid plants, preferably at least 50% or more preferably at least 75% of the obtained plants and/or embryos are dihaploid.

In one embodiment, step (a) comprises adding the HDACi in the culture of isolated microspores, thereby inducing the sporophytic development of the microspores, and subsequently adding the polyamine. For instance, step (a) comprises inducing the sporophytic development of the microspores in a culture medium comprising the HDACi and subsequently adding the polyamine in the culture of isolated microspores.

In another embodiment, the polyamine is added no sooner than the microspores have divided in culture.

In one embodiment, the HDACi is selected from hydroxamic acids, cyclic tetrapeptides, depsipeptides, aliphatic acids, benzamides, electrophilic ketones, and mixtures thereof. The HDACi is for instance selected from suberoylanilide hydroxamic acid (SAHA), trichostatin A (TSA), butyric acid, a butyrate salt, potassium butyrate, sodium butyrate, ammonium butyrate, lithium butyrate, phenylbutyrate, sodium phenylbutyrate, sodium n-butyrate and mixtures thereof. The HDACi is preferably selected from SAHA, TSA and mixtures thereof. SAHA is preferably used at a concentration of from 0.5 to 40 µM and TSA is preferably used at a concentration of from 0.001 to 1.0 µM.

In one embodiment, the polyamine is selected from putrescine, spermidine, spermine, and mixtures thereof. The polyamine is preferably used at a concentration of from 5 to 200 mg/L.

In one embodiment, step (a) comprises contacting the microspores with one or more plant growth regulators selected from auxins, cytokinins, gibberellins, abscisic acid, and mixtures thereof.

According to a particular aspect of the method according to the present invention, step (a) comprises:
(i) culturing the isolated microspores to obtain globular embryos; and
(ii) culturing the globular embryos to obtain elongated embryos;
wherein step (ii) comprises at least one of:
culturing the globular embryos in the presence of an adsorbent material, in particular activated charcoal;
culturing the globular embryos in a multilayer culture system, comprising a liquid phase overlaying a solid phase, in particular a gelified phase;
culturing the globular embryos under agitation, in particular using a rotary shaker; and
culturing the globular embryos in the dark.

Step (ii) can comprise any combination of the features of the above list, in particular two, three or all four of these features.

In a specific embodiment of step (ii) the solid phase comprises an adsorbent material, in particular activated charcoal, more particularly 1000-5000 mg/L of activated charcoal.

In another embodiment, the liquid phase comprises abscisic acid, in particular 1-5 ppm abscisic acid. Alternatively or in addition, the liquid phase comprises one or more polyamine, in particular 5-200 mg/L polyamines.

In one embodiment, the plant material of the donor plant has been obtained through the steps of:
growing a donor plant of the family Cucurbitaceae;
subjecting the donor plant to a stress treatment, in particular a cold shock; and
recovering plant material containing microspores at a developmental stage competent for induction of embryo development.

In one embodiment, the microspores have been isolated from the plant material of the donor plant at a mid-uninucleate to early binucleate stage of development.

In another embodiment, prior to isolation of the microspores from the plant material of the donor plants, the plant material has been collected from the donor plants and has been subsequently subjected to a stress treatment, in particular a cold shock.

In one embodiment, the isolated microspores have been subjected to a stress treatment, in particular a heat shock, prior to step (a).

In another embodiment, the donor plant belongs to the genera *Cucumis, Cucurbita* or *Citrullus*, in particular to the genus *Cucumis*. In particular, the donor plant can belong to the species *Cucumis sativus, Cucumis melo, Cucurbita pepo*, or *Citrullus lanatus*. More particularly, the donor plant can belong to the species *Cucumis sativus* or *Cucumis melo*, still more particularly to the species *Cucumis sativus*. In one embodiment, the donor plant is parthenocarpic. In another embodiment, the donor plant is non-parthenocarpic. In one embodiment the donor plant is selected from a monoecious, dioecious, gynoecious, androecious, andromonoecious, gynomonoecious, hermaphrodite, protoandrous or protogynous plant.

In one embodiment, the method according to the present invention further comprises a step of selecting haploid, dihaploid or haploid and dihaploid plants from the regenerated plants. The step of selecting haploid, dihaploid or haploid and dihaploid plants from the regenerated plants can comprise determining the level of ploidy by flow cytometry. The method according to the present invention can also further comprise a step of analyzing the zygosity of a regenerated plant, preferably by use of one or more molecular markers.

In one embodiment, the method according to the present invention further comprises a step of doubling of the chromosome stocks of the haploid plants regenerated in step (b). For instance, the step of doubling of the chromosome stocks of the haploid plants comprises contacting the haploid plants with a chromosome-doubling agent, in particular colchicine.

In one embodiment, the method according to the present invention further comprises the step of crossing a plant regenerated at step (b) or a doubled haploid plant obtained or obtainable by doubling the chromosome stock of a haploid plant regenerated at step (b), with another plant of the family Cucurbitaceae, in particular of the same species, and obtaining seeds and/or progeny plants, preferably hybrid seeds and/or progeny plants. The plant regenerated at step (b) which is crossed is preferably a dihaploid plant. In one embodiment, the other plant is also a dihaploid plant or a doubled haploid plant, in particular obtained according to the methods of the present invention.

The present invention also relates to a plant obtained or obtainable by the method according to the present invention, or a plant part, cell, seed or progeny thereof. In particular, the plant is haploid, dihaploid, polyhaploid or doubled haploid. More particularly, the plant is haploid, dihaploid or doubled haploid. Still more particularly, the plant is dihaploid or doubled haploid, even more particularly the plant is dihaploid. In one embodiment, the seed or progeny is a F1 hybrid seed or progeny plant. In one embodiment, the plant part or cell is not reproductive material. Alternatively or in addition, the plant part or cell is not capable of maintaining its life through photosynthesis. In another embodiment, the plant is not a variety.

The present invention also relates to a method for producing embryos of the family Cucurbitaceae from isolated microspores, wherein said method comprises:

a) culturing isolated microspores to obtain embryos, wherein the microspores have been isolated from plant material of a donor plant of the family Cucurbitaceae; and wherein step (a) comprises contacting the microspores with one or more inhibitor of histone deacetylase (HDACi) and one or more polyamine.

The present invention also relates to a method for producing plants and/or embryos of the family Cucurbitaceae from isolated microspores, wherein said method comprises:

α) culturing isolated microspores to obtain globular embryos, wherein the microspores have been isolated from plant material of a donor plant of the family Cucurbitaceae;

β) culturing the globular embryos to obtain elongated embryos;

γ) culturing the elongated embryos to obtain torpedo and/or cotyledonary embryos; and δ) regenerating plants from the torpedo and/or cotyledonary embryos, wherein step (a) comprises contacting the microspores with one or more inhibitor of histone deacetylase (HDACi) and one or more polyamine. Depending on whether a plant or an embryo is to be obtained and the stage of embryos to be obtained, step (δ), or steps (γ) and (δ), or steps (β) and (γ) and (δ) can be omitted.

In one embodiment, step (β) comprises at least one of:
culturing the globular embryos in the presence of an adsorbent material, in particular activated charcoal;
culturing the globular embryos in a multilayer culture system, comprising a liquid phase overlaying a solid phase, in particular a gelified phase;
culturing the globular embryos under agitation, in particular using a rotary shaker; and
culturing the globular embryos in the dark.

In one embodiment, step (γ) comprises at least one of:
culturing the elongated embryos in the presence of an adsorbent material, in particular activated charcoal;
culturing the elongated embryos in a multilayer culture system, comprising a liquid phase overlaying a solid phase, in particular a gelified phase;
culturing the elongated embryos under agitation, in particular using a rotary shaker; and
culturing the elongated embryos in the dark.

In one embodiment, step (β) and/or step (γ) comprises culturing the embryos, in particular the globular and/or elongated embryos, under agitation, in a multilayer culture system, comprising a liquid phase overlaying a solid phase comprising an adsorbent material. Preferably step (β) and/or step (γ) comprises culturing the embryos in the dark.

In another embodiment, step (γ) comprises a step of culturing the elongated embryos in or on a solid culture medium, such as a gelified culture medium.

The present invention also relates to a kit for performing a method for producing embryos and/or plants of the family Cucurbitaceae from isolated microspores, wherein said kit comprises one or more HDACi and one or more polyamine, wherein the one or more HDACi and the one or more polyamine are comprised within a same container or within two or more separate containers. In one embodiment, the kit comprises a first composition comprising one or more HDACi and a second composition comprising one or more polyamine. In one embodiment, the first and second compositions are media for plant cell culture. In one embodiment, the first composition is in a first container and the second composition is in a second container. In another embodiment, the kit comprises a composition comprising one or more HDACi and one or more polyamine. In one embodiment, the composition is a medium for plant cell culture. The kit may include a set of instructions for using the HDACi and/or the polyamine. Either or both of the HDACi and polyamine may be in a concentrated form and require dilution prior to use. The kit may further comprise solutions for the dilution of the HDACi and/or polyamine stock solutions that the kit provides. The HDACi and/or polyamine may be provided in dry form and solutions may be provided in the kit for making up solutions. In one embodiment, the kit comprises one or more plant growth regulators selected from auxins, cytokinins, gibberellins, abscisic acid, and mixtures thereof. The one or more plant growth regulators can be comprised in the same container as the HDACi and/or the polyamine or in a separate container. It is for example included in the composition(s) comprising the HDACi and/or polyamine, in particular in a plant cell culture medium comprising the HDACi and/or polyamine. In another embodiment, the kit comprises one or more chromosome doubling agent, such as colchicine, contained in a further container.

The present invention also relates to the use of a kit according to the present invention for producing haploid, dihaploid, polyhaploid and/or doubled haploid plants of the family Cucurbitaceae by androgenesis from isolated microspores.

The present invention also relates to the use of one or more HDACi and one or more polyamine for producing embryos and/or plants of the family Cucurbitaceae by androgenesis from isolated microspores.

DEFINITIONS

Figure 1:
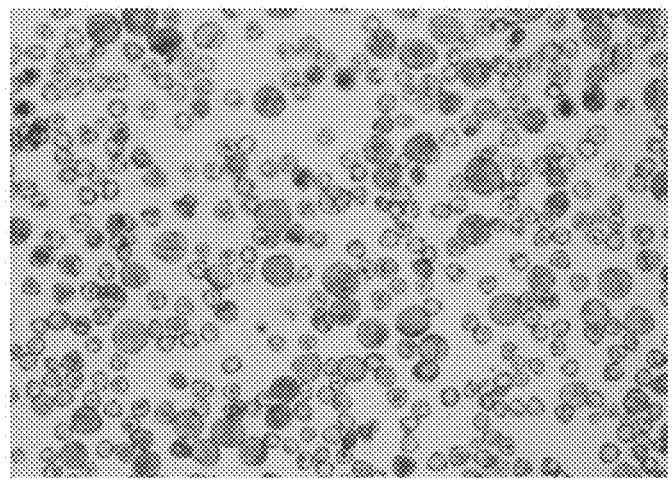
FIG. 1: light microscopy images of microspore cultures induced with SAHA (A) and without SAHA (B).
Figure 1:
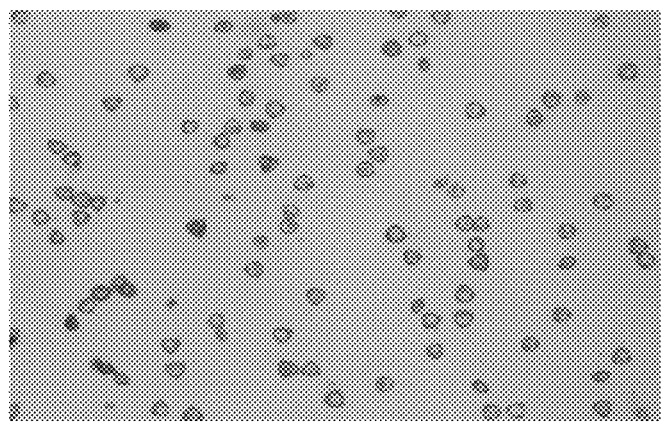

Androgenesis is defined as the process of generation of an individual whose genetic background is derived exclusively from a nucleus of male origin. That is, androgenesis is the generation of a plant exclusively from a male, haploid gamete precursor (gametophyte).

Haploid is an attribute applicable to cells or to plants or parts of plants, of which the chromosomes contained in their nucleus are each in only one copy (n).

Diploid is an attribute applicable to cells or to plants or parts of plants, of which the chromosomes contained in their nucleus are each in two copies (2n).

Doubled haploid is an attribute applicable to cells or to plants or parts of plants comprising said cells, the chromosome stock of which was multiplied artificially, most often by chemical treatment, such as with colchicine. This doubling of the chromosome stock makes it possible to obtain a cell, plant or plant part that has two copies of each chromosome in its nucleus (2n), wherein said cell, plant or plant part is entirely homozygous or essentially homozygous.

Dihaploid is an attribute applicable to cells or to plants or parts of plants comprising said cells, these cells being haploid initially, and their chromosome stock having doubled spontaneously. A dihaploid plant cell, plant or plant part has two copies of each chromosome in its nucleus (2n), and is entirely homozygous or essentially homozygous.

Polyhaploid is an attribute applicable to cells or to plants or parts of plants comprising said cells, these cells being haploid initially, and their chromosome stock having tripled or more spontaneously. The cell, plant or plant part that has at least three copies of each chromosome in its nucleus (3n or 4n etc. . . . ), wherein said cell, plant or plant part is entirely homozygous or essentially homozygous.

Homozygous means a cell or an individual that possesses two identical alleles of one and the same gene on a specified locus of the same chromosome pair, for the characteristic supplied by said gene.

Essentially homozygous means a cell, plant or plant part that possesses identical alleles of the same gene for at least 80%, in particular at least 85%, more particularly at least 90% or at least 95% or at least 99% of the alleles tested.

The term microspore is herein used to designate an immature male gametophyte of a plant at all stages of its in vitro growth, including its multicellular form derived from the sporophytic divisions of a single cell isolated microspore, and still enclosed within the original exine wall (this multicellular form is herein also referred to as a multicellular structure). Hence, the terms "contacting a microspore" or the likes include contacting a single cell isolated microspore as well as contacting a multicellular structure derived from a single cell isolated microspore.

The terms multicellular structure refer to the embryogenic multicellular cluster of cells generated by sporophytic division of an isolated microspore in culture. Due to the random nature of the microspore divisions, the multicellular structures have no evident organization. Multicellular structures are contained in an exine wall, which differentiates them from embryos, which have been released upon breakdown of the exine wall.

As used herein, an embryo refers to a multicellular cluster of cells generated upon breakdown of the exine wall surrounding the multicellular structures, and which can give rise to a plantlet. Embryos go through different stages of development: globular embryos derive from the release of the microspore-derived multicellular structures from their exine wall. Globular embryos can thus consist in a multicellular cluster of cells, with no evident organization, and little similarity to their zygotic counterpart, with the exception of a well-defined protoderm. The globular embryo is normally released upon rupture of the exine wall surrounding the multicellular structures. Globular embryos are subject to a process of histodifferentiation, which involves their elongation, giving rise to elongated embryos. Bilateral symmetry becomes apparent from the heart stage of embryogenesis. In the subsequent torpedo and cotyledonary stages of embryogenesis, the embryo completes its growth by elongating and enlarging.

An embryo competent for plant regeneration designates an embryo which, when cultured in suitable conditions, can be regenerated into a plantlet, and further grown into a plant. The embryo is for example at the torpedo or cotyledonary stage.

Parthenocarpy is the natural or artificially induced production of fruit without fertilization of ovules. A parthenocarpic plant is thus able to produce seedless fruit, which is a valuable trait for edible fruits.

A dioecious plant is a plant having either only male flowers (androecious) or female flowers (gynoecious).

A monoecious plant is a plant having both male and female or bisexual flowers, or both female and male or bisexual flowers. Plants bearing separate flowers of both sexes at the same time are called simultaneously or synchronously monoecious. Plants bearing flowers of one sex at one time are called consecutively monoecious.

An androecious plant is a plant having only male flowers. By extension, a gynoecious plant according to the present application is plant having essentially only male flowers, i.e. it can have a few female or bisexual flowers, e.g. no more than 10% or 5% or 2.5% or 1% female or bisexual flowers.

A gynoecious plant is a plant having only female flowers. By extension, a gynoecious plant according to the present application is plant having essentially only female flowers, i.e. it can have a few male or bisexual flowers, e.g. no more than 10% or 5% or 2.5% or 1% male or bisexual flowers.

A hermaphroditic plant is a plant having bisexual flowers, i.e. flowers having both stamens and carpels.

An andromonoecious plant has both bisexual flowers and male flowers on the same plant.

A gynomonoecious plant has both bisexual flowers and female flowers on the same plant.

A protoandrous plant is a plant having male parts of flowers developed before female parts, e.g. having flowers that function first as male and then change to female or producing pollen before the stigmas of the same plant are receptive.

A protogynous plant is a plant having female parts of flowers developed before male parts, e.g. having flowers that function first as female and then change to male or producing pollen after the stigmas of the same plant are receptive.

A used herein, a molecular marker means a specific fragment of a DNA sequence that can be identified within the genome of an individual and that can notably be used for localizing a gene of interest, verifying if an individual has inherited a particular characteristic from a parent or differentiating two individuals. It may or may not be a coding sequence. Detection of the molecular marker, or its non-detection makes it possible to select the individuals having the gene of interest or the particular characteristic, or, on the contrary, not select the individuals that do not have the gene of interest or the particular characteristic. In the present invention, the molecular markers permit the rapid testing of plants or plantlets during development and retain those that possess the required characteristics. Molecular markers of various kinds are known by a person skilled in the art: AFLP (amplification fragment length polymorphisms), SCAR (sequence characterized amplified region), SSR (microsatellites, simple sequence repeats), RFLP (restriction fragment length polymorphisms), SNP (single nucleotide polymorphism), etc. . . .

Unless otherwise specified or implied by the context, each compound used in the present invention is used in an effective amount, namely an amount sufficient to have a desirable effect under specified conditions. Furthermore, unless otherwise specified or implied by the context, an effective amount in the present specification is an amount sufficient to enable androgenesis.

As described herein, a histone deacetylase inhibitor (HDACi) is a compound which is capable of interacting with a histone deacetylase and inhibiting its enzymatic activity, thereby reducing the ability of a histone deacetylase to remove an acetyl group from a histone.

Acetylation and deacetylation of the lysine residue in histone proteins are often involved in the reversible modulation of chromatin structure in eukaryotes and can mediate the positive-negative regulation of transcription. Histone acetyltransferases catalyze histone acetylation, whilst histone deacetylases (HDAC) catalyze histone deacetylation. Without wishing to be bound by theory, histone deacetylase inhibitors are thus thought to regulate gene transcription by promoting the switch from a condensed form of chromatin to an expanded form.

In some embodiments, the HDACi reduces histone deacetylase activity by at least about 50% or at least about 75%, or at least about 90%, or at least 95%, or at least 99%. Determining whether a compound is a HDACi can be done by using standard enzymatic assays derived from measuring the ability of agent to inhibit catalytic conversion of a substance by the subject protein. In this manner, inhibitors of the enzymatic activity of histone deacetylase proteins can be identified (see Yoshida et al., J. Bio Chem. 265: 17174-17179 (1990)). Examples of HDACi useful in the present invention are disclosed in the following.

As used in the present invention, a polyamine is an organic compound having two or more primary amine moieties —$NH_2$. A polyamine may be linear or cyclic. Polyamines are generally considered as plant hormones and have for example been shown to be involved in modulating senescence of organs in plants. Unless otherwise specified, any mention of a polyamine, in the present specification, such as in "contacting the microspores with one or more polyamine", refers to an exogenous polyamine, e.g. a polyamine added in the culture medium. Examples of polyamines useful in the present invention are disclosed in the following.

It is also noted that, as used in this specification and the appended claims, the singular forms "a," "an," and "the," include plural referents unless expressly and unequivocally limited to one referent. Thus, for example, reference to a HDACi includes two or more different HDACi. As used herein, the term "include" or "comprise" and their grammatical variants are intended to be non-limiting, such that recitation of items in a list is not to the exclusion of other like items that can be substituted or other items that can be added to the listed items. Moreover, unless otherwise specified, reference to a compound, in the present specification, includes all forms of said compound, including a salt, solvate and/or conjugate thereof.

The present invention is based on the unexpected discovery of genotype-independent conditions for culturing Cucurbitaceae microspores and embryos and obtaining plantlets derived therefrom.

Microspore embryogenesis is the process by which an immature male gametophyte gives rise to the development of an embryo, through a series of cellular divisions. Embryogenesis from isolated microspores is usually carried out by collecting microspore-containing material from donor plants, isolating the microspores, culturing the isolated microspores to obtain embryos, and regenerating plants from the embryos.

Donor Plants

The present invention is broadly applicable amongst the Cucurbitaceae family (i.e. cucurbits family). The Cucurbitaceae family is an important family consisting of approximately 98 genera and 975 species, comprising various squashes, melons, and gourds, including crops such as cucumber, zucchinis, pumpkins, luffas, and watermelons. The Cucurbitaceae family comprises two subfamilies Zanonieae and Cucurbitoideae. Subfamily Cucurbitoideae comprises a number of crops, dispersed among several tribes: Melothrieae (*Cucumis sativus, Cucumis melo, Cucumis anguria*); Joliffieae (Momordica charantia); Benincaseae (*Citrullus lanatus, Citrullus colocynthis, Benincasa hispida, Luffa aegyptiaca, Luffa acutangula*); Cucurbiteae (*Cucurbita pepo, Cucurbita maxima, Cucurbita moschata*); and Sicyeae (*Sechium edule*), all of which are herein contemplated for implementing the method according to the present invention.

In certain embodiments, the donor plant is selected from the genera *Cucumis, Cucurbita* and *Citrullus*, more particularly species *Cucumis sativus, Cucumis melo, Cucurbita pepo* and *Citrullus lanatus*, still more particularly *Cucumis sativus*. In one embodiment, the donor plant and is a crop.

Cucumber is a crop of high interest for use of the present invention. Cucumber is one of the vegetable species the most cultivated in the world, after tomato and melon. Practically speaking, all cultivated forms of cucumber belong to the highly polymorphic species *Cucumis sativus* L. that is grown for its edible fruit. As a crop, cucumbers are grown commercially wherever environmental conditions permit the production of an economically viable yield. They can be hand or mechanically harvested.

Cucumbers are consumed in many forms. Cucumbers that are grown for fresh market, also called slicers, are generally hand harvested. Those that are to be processed are called picklers and may be hand or mechanically harvested. Although slicing cultivars may be processed, they generally are not acceptable substitutes for the pickling cucumbers. They are produced on trailing or climbing vines. On healthy plants there is a canopy of large, regular, three lobed leaves, in an alternate arrangement. Pickling cucumbers grown in the United States have usually blunt and angular fruits. They are white-spined and most possess dark green or medium dark green exterior color. Most slicers have slightly rounded ends and taper slightly from the stem to blossom end, although cylindrical-shaped fruits with blocky or even rounded ends are also available. Many changes that occurred with the domestication of the cucumber relate to fruit morphology, with a specialization in fruit shape and size. Slicing cucumbers are frequently sold in lengths from 6 to 10 in (15.2 to 25.4 cm), and diameter varies from 1.5 in (3.8 cm) to nearly 3 in (7.9 cm). In the United States, the principal slicer cucumber growing regions are Georgia, Florida, Michigan, California and North Carolina with nearly 42,000 acres (16,996 ha) out of a US total acreage of 57,500 acres (23269 ha). The main states that produce processing cucumbers are Michigan, North Carolina and Texas. Fresh cucumbers are available in the United States mainly from spring to fall.

Beit alpha cucumbers are grown both indoors (greenhouse, parthenocarpic) and outdoors in the open field primarily throughout Turkey and the Middle East. Beit alpha's tend to be cylindrical, spineless and without tubercles, medium ribbed/textured, and medium to dark green in color, but it is common to see slight variation in all of these traits. Fruit length ranges from 14 to 22 cm, with 16-18 cm being the most common and preferred, with a diameter typically 2.5 to 4 cm. Length is a trait which can be significantly affected by environmental conditions and growing region. Most commonly, beit alpha cucumbers are used fresh, and are typically eaten with all meals in their primary markets. There are some beit alpha cucumbers used for processing into pickles. This is typically with fruit picked very small, around 8 cm in length.

European market types include glasshouse cucumbers, Mediterranean or "Mini" types for glasshouse or poly-tunnel production, and processing cucumbers (i.e. gherkins). Mini cucumbers have 14-17 cm long fruit. European glasshouse types (32 to 40 cm long) are gynoecious, parthenocarpic (seedless), resistant to diseases such as powdery mildew (Sphaerotheca fuligines (Schl. Ex Fr.) Poll.), and cucumber mosaic, virus (CMV) and will produce fruit under controlled climate conditions where commercial production is an exacting a costly enterprise.

Some representative cultivars in Europe as well as in the U.S. and Canada include 'Jessica', 'Optima', 'Flamingo', 'Toska 70', 'Averyl', 'Niagara', 'Ladner', 'Sandra', 'Camaro', 'Dominica', 'Bella', 'Activa', and 'Sinaloa'. Some typical, disease resistant gynoecious, mini cultivars are 'Jawell', 'Manar', 'Alamir', and 'Melita'.

The donor plant preferably has one or more traits of agricultural interest, in particular resistance to a disease, the capacity for adaptation to abiotic stress, in particular adaptation to an acidic soil, a hydromorphic soil, a cold soil, a lack of water or saline stress, a morphological characteristic such as the colour or the shape of the fruits, in particular the length and/or diameter of the fruits, the presence, quantity or morphology of the seeds in the fruits, the nutrient composition or a gustatory characteristic of the fruits, fruit resistance to injuries.

The donor plant is preferably resistant to a disease selected from viruses such as Cucumber mosaic virus (CMV), Watermelon mosaic virus (WMV), Zucchini Yellow Mosaic Virus (ZYMV), green mottle mosaic virus, gummy stem blight, phytophthora rot, Cucumber Vein Yellowing Virus, diseases caused by fungi such as scab, powdery mildew, downy mildew, anthracnose or fusarium, diseases caused by bacteria such as bacterial wilt or angular leaf spot, or diseases caused by insects such as root knot nematodes. The donor plant may cumulate two or more of the above mentioned resistances.

In one embodiment, the donor plant is a non-fixed line. In particular, the donor plant can be a F1 hybrid.

In the present invention, the donor plant can be monoecious, dioecious, gynoecious, androecious, andromonoecious, gynomonoecious, hermaphrodite, protoandrous or protogynous. A completely gynoecious plant can be used as a microspore donor by being converted to a male plant. This process is carried out, for example, by treating the plants with an inhibitor of ethylene receptor such as silver thiosulfate or other heavy metal compounds. The conversion is temporary and plants will revert back to their normal phenotype after some time depending on dosage. The plant regenerated according to the methods of the present invention will normally also be gynoecious, as this trait is determined genetically.

Moreover, the present invention is applicable to parthenocarpic plants and non-parthenocarpic plants.

Collection of Microspore-containing Material and Isolation of the Microspores

The donor plants can be cultivated in the field, but are preferably cultivated in a controlled environment that is less contaminated with microorganisms, such as a greenhouse.

The plants are cultivated until budding, and plant material containing microspores, in particular buds or portions of buds containing microspores, e.g. anthers, are collected. Any plant material can be collected as long as it contains microspores which are amenable to embryogenesis. The plant material, in particular buds, can be collected at any time of plant life cycle. Peak production of buds is a preferred time for bud collection, as it will provide buds in higher quantity and quality. The plant material is preferably collected in the morning, at a time which maximizes the quantity of buds containing microspores at a developmental stage amenable to embryogenesis. The microspores, when collected from the donor plant, are preferably at a mid-uninucleate to binucleate developmental stage, more particularly a mid-uninucleate or mid-to-late uninucleate to early binucleate developmental stage. The majority of microspores is preferably at the late uninucleate stage. In certain embodiments, at least 60%, in particular at least 70%, more particularly at least 80%, still more particularly at least 90% of the microspores is at the late uninucleate stage.

In certain embodiments, the donor plants are subjected to a stress treatment before collection of the plant material. The present inventors have shown that a stress treatment, in particular a cold shock applied to the donor plant, before bud collection, can increase the efficiency of microspores to produce embryos. In certain embodiments, the stress treatment is a nutrient treatment, a light treatment or a temperature treatment, in particular a heat shock or a cold shock. The stress treatment is preferably a temperature treatment, still preferably a cold shock. The cold shock is applied, for instance, by subjecting the donor plants to a temperature of 4-16° C., in particular 5-12° C., more particularly 6-10° C., still more particularly about 8° C. In one embodiment, the cold shock is applied for from 1 hour to 6 days, preferably from 12 hours to 4 days, still preferably from 24 to 72 hours. The cold shock is not necessarily followed immediately by collection of the plant material, e.g. buds, and, in certain embodiments, a period of time can be waited between the end of the cold shock and bud collection, e.g. no more than 24 hours. Preferably, the plant material is collected immediately or essentially immediately after the end of the cold shock, e.g. no more than 1 hour after the end of the cold shock. In one embodiment, the plant material is collected whilst the donor plants are still exposed to the cold shock. In another embodiment, the plant material is collected in the morning, and the period of cold shock application includes the night preceding bud collection.

Once collected, the plant material is subjected to a treatment which includes its disinfection to remove any microorganism or pest liable to infest the culture of isolated microspores.

In certain embodiment, the collected plant material is subjected to a stress treatment before or after disinfection. Indeed, a stress treatment, such as a cold shock applied to collected buds has been demonstrated to improve androgenesis. In certain embodiments, the stress treatment is a nutrient treatment, a light treatment or a temperature treatment, in particular a heat shock or a cold shock. The stress treatment is preferably a temperature treatment, still preferably a cold shock. The cold shock is applied, for instance, by exposing the collected plant material to a temperature of 0-8° C., in particular 2-6° C. In one embodiment, the cold shock is applied for from 1 hour to 6 days, preferably from 12 hours to 5 days, still preferably from 24 hours to 4 days.

The microspores are then isolated from the collected plant material by any suitable process, for example comprising blending, macerating or otherwise breaking down the surrounding tissue, and one or more steps of filtering the ground material through a screen mesh size sufficient to separate the microspores and the undesirable material, such as debris or particles of surrounding tissues etc. . . . . The isolated microspores are preferably obtained as a suspension of cells at 30,000-150,000 cells/mL.

Culture of the Microspores

Once isolated, the microspores are cultured under conditions enabling their development into embryos competent for plant regeneration. This step can comprise the substeps of:

(i) culturing the isolated microspores to obtain globular embryos; and (ii) culturing the globular embryos to obtain elongated embryos.

In certain embodiments, the microspores are exposed to a stress treatment before culture or at the onset of the culture. The present inventors have surprisingly discovered that a stress treatment, in particular a heat shock applied to the isolated microspores, before their culture or at the onset of the culture, can increase the efficiency of embryogenesis from the cultured microspores. In certain embodiments, the stress treatment is a nutrient treatment, an osmotic treatment, a light treatment or a temperature treatment, in particular a heat shock or a cold shock. In a preferred embodiment, the stress treatment is a heat shock. The heat shock is applied, for instance, by exposing the microspores to a temperature of at least at least 3° C., or at least 4° C. or at least 5° C. higher than the temperature of culture of the isolated microspores (i.e. the temperature of the subsequent culture step). In particular, the heat shock temperature is from 3 to 10° C. higher than the temperature of culture of the isolated microspores, preferably from 2 to 9° C. higher than the temperature of culture of the isolated microspores, still preferably from 5 to 8° C. higher than the temperature of culture of the isolated microspores. In one embodiment, the heat shock temperature is of 28-35° C. or 28-33° C., in particular 29-34° C. or 29-33° C., more particularly 30-33° C., still more particularly about 30° C. In one embodiment, the heat shock is applied for from 1 hour to 6 days, preferably from 12 hours to 4 days, still preferably from 24 to 72 hours. The heat shock is preferably applied in the dark.

(i) Culture of the isolated microspores to obtain globular embryos

In step (i), the isolated microspores are cultured under conditions enabling their development into globular embryos. Step (i) can comprise the substeps of:

culturing the isolated microspores into multicellular structures. In this step, the isolated microspores are cultured under conditions enabling their development into multicellular structures; and culturing the multicellular structures into globular embryos. In this step, the multicellular structures are cultured under conditions enabling their development into globular embryos.

The first stage of microspore embryogenesis is the induction of the sporophytic growth of the microspores. In a plant, the normal development of a microspore consists in undergoing a series of two mitotic divisions to form the mature trinucleate male gametophyte, i.e. the mature pollen grain: this is the gametophytic pathway. However, upon exposure to suitable conditions, isolated microspores in culture can switch from the gametophytic pathway of development to the sporophytic pathway.

The present inventors have discovered that contacting isolated microspores of the Cucurbitaceae family with one or more histone deacetylase inhibitor (HDACi) can promote the induction of the sporophytic pathway. HDACi are thus used as an inducer of sporophytic development. HDACi can also be kept contacting with the culture at later stages of the microspore culture, e.g. with sporophytically-divided microspores, i.e. multicellular structures and/or with microspore-derived embryos.

The present inventors have also surprisingly discovered that the action of HDACi, although necessary, was not sufficient to induce normal embryogenesis from isolated microspores of the family Cucurbitaceae. Indeed, when the microspores are cultured with only HDACi, and without polyamine in the culture medium, they tend to develop into abnormal embryoid structures, which will not be capable to be regenerated into plants. By contrast, addition of polyamine in the culture medium, for example when the microspores have already undergone sporophytic divisions in culture, will help to induce a normal development of the embryos. This effect of polyamine is particularly unexpected, as other compounds have been tested by the present inventors in combination with an HDACi, and have failed to lead to a successful embryogenesis (see Example 3). These conditions of culture including the use of an HDACi, or a mixture of HDACi and a polyamine, or a mixture of polyamines, are genotype-independent or essentially genotype-independent. To the inventors' knowledge, it is the first time that genotype-independent conditions for induction of embryogenesis from Cucurbitaceae isolated microspores are identified.

In one embodiment, the method is carried out on a microspore population comprising at least 200 microspores, preferably at least 500 microspores, still preferably at least 1000 microspores, further still preferably at least 5000 microspores, still more preferably at least 10000 microspores.

In one embodiment, at least 0.1%, preferably at least 0.2%, still preferably at least 0.5% of the cultured microspores develop into multicellular structures. In another embodiment, at least 0.1%, preferably at least 0.2%, still preferably at least 0.5% of the cultured microspores develop into microspore-derived embryos.

The HDACi can be any molecule that effects a reduction in the activity of a histone deacetylase. This includes proteins, peptides, DNA molecules (including antisense), RNA molecules (including RNAi and antisense) and small molecules. A protein may be an antibody, monoclonal, polyclonal or chimeric; and a peptide may be a fragment of such an antibody. HDACi include for example the following classes of compounds: hydroxamic acids, cyclic tetrapeptides, depsipeptides, aliphatic acids, benzamides, polyphenols or electrophilic ketones.

Hydroxamic acid-based HDACi useful in the present invention include hydroxamic acid-based hybrid polar compounds (HPCs), such as suberoylanilide hydroxamic acid (SAHA), suberyl bishydroxamic acid (SBHA); salicyl hydroxamic acid; azelaic bishydroxamic acid (ABHA); azelaic-1-hydroxamate-9-anilide (AAHA); M-carboxycinnamic acid bishydroxamide (CBHA); 6-(3-chlorophenylureido)carpoic hydroxamic acid (3-CI-UCHA); MW2796 (Andrews et al, International J. Parasitology. 30, 761-768 (2000); and MW2996 (Andrews et al., supra). In one embodiment, the HDACi compound is not salicyl hydroxamic acid.

Other hydroxamic acid-based HDACi useful in the present invention include trichostatin A (TSA), and compounds related to TSA, such as M344 which is an amide analog of TSA and analogues disclosed in US 2011/0237832.

Further example of hydroxamic acids useful in the present invention include oxamflatin ((2E)-5[3-(Phenylsulfonylamino)phenyl]-pent-2-en-4-ynohydroxamic acid).

Examples of cyclic tetrapeptide with an HDACi activity include trapoxin, in particular trapoxin A (TPX) (cyclo-(L-phenylalanyl-L-phenylalanyl-D-pipecolinyl-L-2-amino-8-oxo-9,10-epoxy decanoyl)); FR225497 (H. Mori et al., PCT Application WO 00/08048) ; apicidin [cyclo (N-O-methyl-L-tryptophanyl-L-isoleucinyl-D-pipecolinyl-L-2-amino-8oxodecanoyl)] (Darkin-Rattray et al., Proc. Natl. Acad. Sci. USA 93,1314313147 (1996)); apicidin Ia, apicidin Ib, apicidin Ic, apicidin IIa, and apicidin IIb (P. Dulski et al., PCT Application WO 97/11366); CHAP, HC-Toxin (Bosch et al., Plant Cell 7, 1941-1950 (1995)) ; WF27082 (PCT Application WO 98/48825); and Chlamydocin (Bosch et al., supra).

The HDACi can also be a depsipeptide, for example romidepsin or spiruchostatin A.

Exemplary aliphatic acids which can be used as an HDACi include, but are not limited to short chain fatty acid derivatives, such as sodium butyrate (Cousens et al., J. Biol. Chem. 254, 1716-1723 (1979));isovalerate (McBain et al., Biochem. Pharm. 53: 1357-1368 (1997)); valerate (McBain et al., supra); 4-phenylbutyrate (4-PBA) (Lea and Tulsyan, Anticancer Research, 15, 879-873 (1995)) ; phenylbutyrate (PB) (Wang et al., Cancer Research, 59, 2766-2799 (1999)); propionate (McBain et al., supra); butyramide (Lea and Tulsyan, supra); isobutyramide (Lea and Tulsyan, supra); 3-bromopropionate (Lea and Tulsyan, supra); tributyrin (Guan et al., Cancer Research, 60, 749-755 (2000)); valproic acid and valproate.

Examples of benzamide useful as an HDACi include, but are not limited to CI-994; MS-27-275 [N-(2-aminophenyl)-4-[N-(pyridin-3-yl methoxycarbonyl) aminomethyl] benzamide] (Saito et al., Proc. Natl. Acad. Sci. USA 96, 4592-4597 (1999)); and 3'-amino derivative of MS-27-275 (Saito et al., supra).

Electrophilic ketones which act as HDACi include, but are not limited to trifluoromethyl ketones (Frey et al, Bioorganic & Med. Chem. Lett. (2002), 12, 3443-3447; U.S. Pat. No. 6,511,990) and α-keto amides such as N-methyl-α-ketoamides.

Polyphenolic HDACi include naturally occurring plant polyphenols, for example epigallocatechin-3-gallate (EGCG) and genistein (GEN) as well as oxidative methyleugenol (ME) metabolites.

Natural products with HDACi activity are available and may be used in accordance with the invention, including: curcumin, butyrate, diallyl disulphide, sulfopropane and parthenolide.

Further examples of HDACi compounds include rocilinostat (ACY-1215); etinostat (MS-275); mocetinostat (MGCD0103, MG0103); belinostat (PXD101); dacinostat (LAQ824); droxinostat (CMH, 5809354); resminostat (RAS2410); panobinostat (LBH589); pracinostat (SB939); givinostat (ITF2357); quisinostat (JNJ-26481585); abexinostat (PCI-24781).

Still further examples of HDACi include depudecin (Kwon et al. 1998. PNAS 95: 3356-3361), and Scriptaid (Su et al. 2000 Cancer Research, 60:3137-42), cambinol, tubacin, tubastatin, resveratrol, resveratrol (3,4',5-Trihydroxy-frans-stilbene); splitomicin (1,2-Dihydro-3H-naphtho[2,1-b]pyran-3-one); tacedinaline (CI994); sulindac; PXD101; PTACH S-[6-(4-Phenyl-2-thiazolylcarbamoyl)hexyl] thioisobutyrate; CUDC 101 (7-[[4-(3-Ethynyl phenylamino)-7-methoxyquinazol in-6-yl]oxy]-N-hydroxyheptanamide); MOCPAC (Benzyl (S)-[1-(4-methyl-2-oxo-2H-chromen-7-ylcarbamoyl)-5-propionylam inopentyl] carbamate); MC1568; PCI-34051; CI-994 (4-Acetylamino-N-(2'-aminophenyl)benzamide); CUDC-101; CUDC-907; LAQ 824; AR-42 (OSU-HDAC42); APHA Compound 8 (3-(1-Methyl-4-phenylacetyl-1H-2-pyrrolyl)-N-hydroxy-2-propenamide); BATCP (N-[(1S)-5-(Acetylamino)-1-[[[2-oxo-4-(trifluoromethyl)-2H-1-benzopyran-7-yl]amino]carbonyl]pentyl] carbamic acid tert-butyl ester); MGDCD0103; SB939; CHR-2845; CHR-3996; 4SC-202; Sulforaphane; Kevetrin.

Other examples of HDACi molecules include proteins and peptides, including antibodies or fragments thereof, preferably monoclonal antibodies that specifically react with the histone deacetylase.

In certain embodiments, the HDACi is not salicyl hydroxamic acid, or is not phenylacetic acid. In other embodiments, the HDACi is not a polyamine. In still other embodiments, the HDACi is not an auxin. In still other embodiments, the HDACi is not a cytokinin. In still other embodiments, the HDACi is not a gibberelin. In still other embodiments, the HDACi is not a chromosome doubling agent.

Preferred HDACi include SAHA, TSA, and salts, analogues and derivatives thereof. SAHA is particularly preferred.

In the practice of the invention, an effective amount of HDACi is used. In particular, a sufficient amount of HDACi is employed to effect a measurable induction of sporophytic development. Suitable amounts will vary depending on the specific inhibitor. The concentration range of HDACi in the culture medium may therefore be from about 0.001 nM to about 100 mM; preferably a range selected from one of the following: from about 0.01 nM to about 50 mM; from about 0.05 nM to about 10 mM; from about 0.1 nM to about 5 mM; from about 0.5 nM to about 1 mM; from about 1 nM to about 500 µM; from about 5 nM to about 250 µM; from about 10 nM to about 100 µM; from about 25 nM to about 50 µM. Non-limiting examples of concentration useful for the present invention are 0.05 µM to 500 µM, preferably 0.1 to 200 µM, still preferably 0.25 to 100 µM, still more preferably 0.50 to 40 µM SAHA. In particular 1 to 30 µM, more particularly 2 to 20 µM, still more particularly 5 to 15 µM, for instance about 10 µM SAHA can be used. Other non-limiting examples of useful concentrations of HDACi are 0.001 to 5 µM, preferably 0.001 to 2.5 µM, still preferably 0.001 to 1.0 µM of TSA. In particular, 0.01 to 1.0 µM, more particularly 0.1 to 1 µM, for instance about 0.5 µM TSA can be used. Useful concentrations for other HDACi compounds will be readily inferred and assessed by the skilled person, for instance taking into account the relative inhibition potencies of the HDACi compounds.

According to the present invention, the culture of isolated microspores is also preferably contacted with one or more polyamine, at any stage of the culture, including single-cell microspores, multicellular structures and/or embryos. Polyamines, in combination with a HDACi, promote the development of normal embryogenic structures, which are capable to be regenerated into plants.

Non-limiting examples of polyamines useful in the present invention include aliphatic polyamines, in particular tetramethylenediamines such as putrescine, spermidine and spermine. Mixtures of polyamines are particularly preferred, in particular mixtures which comprise putrescine, spermidine and/or spermine. In one embodiment, the polyamine mixture comprises a ratio spermine:putrescine of no more than 1:1, in particular 1:100 to 1:1, more particularly 1:30 to 1:3, still more particularly 1:20 to 1:5, even more particularly about 1:10. In another embodiment, the polyamine mixture comprises a ratio spermidine:putrescine of no more than 1:1, in particular 1:100 to 1:1, more particularly 1:30 to 1:3, still more particularly 1:20 to 1:5, even more particularly about 1:10.

In the practice of the invention, an effective amount of polyamine is used. In particular, a sufficient amount of polyamine is employed to effect a measurable effect on embryogenesis from the isolated microspores, more particularly to increase the rate of development of normal embryos from the isolated microspores, in particular embryos competent for plant regeneration, compared with the same conditions without polyamine. Suitable amounts may vary depending on the specific polyamine. The concentration range may therefore be from about 0.01 mg/L to about 10 g/L; preferably a range selected from one of the following: from about 0.1 mg/L to about 5 g/L; from about 0.5 mg/L to about 2.5 g/L; from about 1 mg/L to about 1 g/L; from about 2 mg/L to about 500 mg/L; from about 5 mg/L to about 200 mg/L. In particular, at least 20 mg/L, more particularly at least 30 mg/L, or at least 50 mg/L or at least 70 mg/L polyamines are used, for example from 20 to 200 mg/L or from 30 to 200 mg/L or from 50 to 200 mg/L. A concentration of about 100 mg/L putrescine is particularly useful in the present invention. In terms of molar concentration, concentrations of more than 200 µM, in particular at least 300 µM, more particularly at least 400 µM, still more particularly at least 500 µM can be preferred. Also, concentrations of no more than 2 mM or 1.5 mM or 1 mM can be preferred, e.g. 300 µM to 2 mM or 500 µM to 2 mM.

In specific embodiments, the steps of contacting the microspores with one or more HDACi and contacting the microspores with one or more polyamines are carried out according to a particular sequence. The present inventors have indeed obtained a higher rate of embryogenesis when the isolated microspore cultures are started with a polyamine free culture medium, and polyamine is added subsequently. The inventors have nevertheless succeeded in obtaining viable embryos when polyamine is added from day 0 of the culture.

Accordingly, in a preferred embodiment, the polyamine is added to the culture of isolated microspores after the HDACi. In particular, the polyamine is added to the culture of microspores at least 1 day after the HDACi, more particularly at least 3 days after the HDACi, still more particularly at least 7 days after the HDACi, and even more particularly from 7 to 10 days after the HDACi. In certain embodiments, the HDACi is contacted with the microspores from day 0 of culture, and the polyamine is contacted with the microspores at least from day 1, more particularly at least from day 3, still more particularly at least from day 7, and even more particularly from day 7 to 10 of culture of the microspores. In one embodiment, the microspores are first cultured in a culture medium comprising the HDACi and without polyamine, and polyamine is added in the same culture medium. In another embodiment, the microspores are first cultured in a first culture medium comprising the HDACi and without polyamine, and the culture medium is replaced by a second culture medium comprising polyamine. In one embodiment, the second culture medium comprises one or more HDACi. In another embodiment, the second culture medium is free of HDACi. In other terms, the polyamine may be further added to the HDACi or may replace the HDACi. Preferably, the polyamine is further added to the HDACi.

The step of contacting the microspore with the polyamine can also be triggered according to the stage of development of the microspores. In certain embodiments, HDACi is contacted with the microspores to induce their sporophytic growth, and polyamine is contacted with the microspores once the sporophytic growth of the microspores has been induced. For instance, the microspores are contacted with polyamine when the microspores have divided in culture. The one or more polyamines are thus preferably added in the microspore culture when the microspores have undergone a few divisions in culture, in particular at least 2, 3, 4, 5, 6, 7, 8, 9, 10 or divisions. In other terms, polyamine is contacted with the microspores when the microspores have developed into multicellular structures. This does not mean necessary that all microspores in the culture have divided or have undergone the specified number of divisions. Indeed, the microspores may respond differently to the HDACi treatment which initiates their sporophytic growth and may thus have different paces of growth in culture. Some of them may also be insensible to this treatment and may never divide. Hence, in one embodiment, polyamine is added when a portion of the microspores have divided in culture, in particular at least 0.1%, 0.5%, 1%, 2%, 3%, 4%, 5%, 6%, 7%, 8%, 9% of the microspores have divided in culture. More particularly, polyamine is added when at least 10%, more particularly at least 20% or at least 30% or at least 40%, or at least 50%, or at least 60%, or at least 70%, or at least 80%, or at least 90% or at least 95% of the microspores have divided in culture.

In another embodiment, the polyamine is contacted with the microspores together with the HDACi, in particular from day 0 of culture.

The medium for culturing the isolated microspores can comprise further components, provided that their presence does not disrupt embryogenesis, i.e. the development of viable embryos from the isolated microspores. Preferably, the further components do not interfere detrimentally with the action of the polyamine and/or HDACi.

In certain embodiments, the microspores are further contacted with one or plant growth regulators. The plant growth regulators include, but are not limited to auxins, cytokinins, gibberellins, abscisic acid, and mixtures thereof. These compounds are generally used in an amount sufficient not to disrupt embryogenesis.

Representative examples of auxins useful in the practice of the present invention include, but are not limited to, phenylacetic acid (PAA) and 2,4-dichlorophenoxyacetic acid (2,4-D), and related auxins such as indoleacetic acid (IAA), indolebutyric acid (IBA), naphthalene acetic acid (NAA). Preferred auxins are 2,4-D, PAA and mixtures thereof.

Representative examples of cytokinin useful in the practice of the present invention include, but are not limited to, 6-benzyladenine (BA or 6-BA), trans-zeatin and trans-zeatin-riboside.

Representative examples of gibberellins useful in the practice of the present invention include GA1, GA3, GA4, and GA7.

Whenever included in the culture medium, a plant growth regulator is used in an effective amount. The concentration range of the plant growth regulator used will vary depending on the specific compound. The concentration range may therefore be from about 0.01 µg/L to about 10 g/L; preferably a range selected from one of the following: from about 0.1 µg/L to about 5 g/L; from about 0.5 µg/L to about 2.5 g/L; from about 1 µg/L to about 1 g/L; from about 5 µg/L to about 500 mg/L; from about 10 µg/L to about 250 mg/L; from about 50 µg/L to about 100 mg/L; from about 100 µg/L to about 75 mg/L; from about 250 µg/L to about 50 µg/L.

Non-limiting examples of concentrations of auxins useful in the present invention include, but are not limited to 0.05 to 500 mg/L, preferably 0.1 to 100 mg/L, still preferably 0.5 to 50 mg/L PAA and/or 0.005 to 20 mg/L, preferably 0.01 to 10 mg/L, still preferably 0.05 to 2 mg/L 2,4-D. Non-limiting examples of concentrations of cytokinins useful in the present invention include, but are not limited to 0.005 to 20 mg/L, preferably 0.01 to 10 mg/L, still preferably 0.05 to 2 mg/L BA.

Preferably, the plant growth regulator is not ethylene.

Other components which can be included in the microspore culture medium include carbohydrates (e.g. maltose, sucrose and fructose), nutrients (in particular macronutrients, e.g. sources of N, P, K, Ca, Mg and S, and micronutrients, e.g. sources of Fe, Ni, Cl, Mn, Zn, B, Cu and Mo), vitamins (in particular thiamine, pyridoxine, nicotinic acid and myo-inositol), amino acids or sources of amino acids, and/or adsorbent materials, in particular activated charcoal. Activated charcoal is for example included at a concentration of 10-100 mg/L in the culture medium. Without wishing to be bound by theory, activated charcoal, along with other adsorbent materials, has the capacity to adsorb toxic and/or inhibitory substances present in the culture medium. Activated charcoal is for example capable of trapping gases, especially ethylene, released from cultured tissues. It is also possible that activated charcoal may exert a beneficial effect by gradually releasing certain products that it has previously adsorbed.

In a particular embodiment, the culture medium used for culturing the microspores comprises or consists of an aqueous mixture of HDACi, polyamine, micronutrients (Fe, Ni, Cl, Mn, Zn, B, Cu and Mo), macronutrients (e.g. sources of N, P, K, Ca, Mg and S), vitamins (e.g. thiamine, pyridoxine, nicotinic acid and myo-inositol), carbohydrates (e.g. maltose, sucrose and fructose) and one or more optional components selected from plant growth regulators, (e.g. auxins, cytokinins, gibberellins, abscisic acid), adsorbent materials (e.g. activated charcoal) amino acids or a source thereof, and buffers.

In one embodiment, the culture medium used for culturing the microspores is based on a basal culture medium such as a Murashige & Skoog (MS)-derived medium. In a specific embodiment, the basal culture medium is a M404 medium (PhytoTechnology Laboratories®). Some of the above components can be comprised in the basal culture medium, whilst other will be added to the basal culture medium.

According to specific embodiments, the step of culturing isolated microspores to obtain embryos competent for plant regeneration, comprises a step of culture in an induction culture medium, thereby enabling the induction of the sporophytic growth of the isolated microspores, and a step of culture in a development culture medium, thereby enabling the development of embryos from the microspores. In preferred embodiments, the induction culture medium is replaced by the development culture medium from at least day 1 of culture, in particular from at least day 3 of culture, more particularly from at least day 7 of culture, still more particularly from day 7 to 10 of culture.

The induction culture medium and the development culture medium can comprise any of the aforementioned compounds in the aforementioned amounts, in particular the HDACi and polyamine compounds.

In some embodiments, the induction culture medium comprises one or more HDACi and one or more polyamine. It is however preferred that the induction culture medium be free of polyamine.

In some embodiment; the development culture medium comprises one or more polyamines. In some embodiments, the development culture medium comprises one or more HDACi. In particular, the development culture medium comprises one or more polyamines and one or more HDACi.

In some embodiments, the development culture medium has the same or a substantially similar composition as the induction culture medium. In other embodiments, the development culture medium has the same or a substantially similar composition as the induction culture medium except for the presence of one or more polyamines in the development culture medium.

Further preferred conditions for the isolated microspore culture include culture in the dark and/or culture at a temperature of 22-28° C.

(ii) Elongation of the Embryos

Culture of the microspores under suitable conditions as described in the present disclosure generally results in the development of globular embryos. Globular embryos are then cultured under conditions effective to let them undergo histodifferentiation, i.e. transition to torpedo and cotyledonary embryos. This histodifferentiation normally involves a stage of elongation of the globular embryos, under suitable conditions. Hence, the culture conditions are generally changed when the microspores have developed into globular embryos. Preferably, the culture conditions for elongation of globular embryos are implemented from at least 20 days, in particular from 20 to 40 days of culture.

In some embodiments, the globular embryos are cultured in the presence of an adsorbent material, in particular activated charcoal.

Some adsorbent materials, such as activated charcoal, can themselves be toxic or have an inhibitory effect for the cultured embryos, when they are used in high quantity. It is thus preferred that a significant portion of the adsorbent material does not contact directly the embryos. Hence, in one embodiment, a majority of the adsorbent material is prevented from contacting the embryos. For instance, at least 50 wt %, preferably 75 wt %, still preferably at least 90 wt %, still more preferably at least 95 or 99 wt % of the adsorbent material is prevented from directly contacting the embryos. To prevent direct contact between the adsorbent material and the embryos, the adsorbent material can be embedded within a solid phase, such as a gelified phase made, for example, of agar. This can be carried out, for instance, through the use of a double layer culture system. The lower layer consists of a solid phase, e.g. a gelified phase comprising the adsorbent material. This phase is for instance based on a gelified culture medium, herein designated as a solid embryo culture medium (SECM). The upper layer consists of a liquid culture medium comprising the embryos, herein designated as liquid embryo culture medium. (LECM). In this way, the embryos are cultured within the LECM, or float on top of it, but do not contact directly the activated charcoal. At the same time, the substances present in the LECM, such as the toxic and/or inhibitory substances released by the cultured embryos, fall onto the solid phase and are adsorbed onto the adsorbent material.

The adsorbent material is used in an effective amount. It is particularly employed in an amount sufficient to enable the elongation of the embryos. In a preferred embodiment, the solid phase comprises at least 100 mg/L activated charcoal, in particular at least 200 mg/L, more particularly at least 500 mg/L, still more particularly at least 1000 mg/L activated charcoal. In another embodiment, the solid phase comprises from 100 to 10,000 mg/L, in particular from 1000 to 5000 mg/L activated charcoal. Optionally, the liquid phase comprises from 10 to 100 mg/L activated charcoal.

In one embodiment, the LECM comprises one or more HDACi and/or one or more polyamines, preferably both HDACi and polyamine. The HDACi and/or the polyamine can be selected from the above lists, and can be present in any of the aforementioned quantities, in the LECM. In certain embodiments, the LECM further comprises plant growth regulators, in particular selected from auxins, cytokinins, gibberellins, abscisic acid, and mixtures thereof. In a preferred embodiment, the LECM comprises abscisic acid, in an amount effective to enable the development of the embryos. In particular, the LECM comprises from 0.5 to 5 ppm abscisic acid, still preferably from 1 to 2 ppm abscisic acid. Abscisic acid and polyamines have been shown by the inventors to have a positive effect on elongation of the embryos.

In some embodiments, the SECM comprises one or more polyamines, e.g. selected from the above lists, and in any of the aforementioned quantities. In some embodiments, the SECM further comprises plant growth regulators, in particular selected from auxins, cytokinins, gibberellins, abscisic acid, and mixtures thereof. In some embodiments, the SECM does not comprise phenylacetic acid (PAA). In other embodiments, the SECM does not comprise HDACi.

Other parameters can assist the elongation of globular embryos, for example agitation of the cultures. Agitation is for example carried out using a rotary shaker at 30-90 rpm, preferably 50-70 rpm. Elongation of the globular embryos can also be assisted by culturing the embryos in the dark.

Any of the conditions of culture described above for elongation of globular embryos can be maintained throughout the differentiation of the embryos, until or during the torpedo stage and up to the cotyledonary stage of the embryos. Preferably, the elongation conditions of cultures are maintained for at least 20 days, for example from 20 to 45 days, for example for about 30 days.

Plant Regeneration

Methods for regenerating plants from differentiated embryos, such as torpedo and cotyledonary embryos are known by the persons skilled in the art. For example, the cotyledonary embryos are subcultured onto an embryo normalization medium until normal plantlets formation, when visible elongation and differentiation of roots and meristem regions are visible. The plantlets can then be placed under conditions of reduced light and high humidity, to promote rooting, for example for 1 to 6 days, preferably 3 to 4 days. The plantlets are then transferred into greenhouses for acclimation steps and grown into plants.

The plants regenerated from the embryos can comprise haploid, dihaploid, polyhaploid plants, aneuploid and/or alleuploid plants. In one embodiment, the plants regenerated from the embryos comprise dihaploid, polyhaploid plants, aneuploid and/or alleuploid plants, in particular dihaploid and polyhaploid plants. In another embodiment, the plants regenerated from the embryos comprise haploid, dihaploid, aneuploid and/or alleuploid plants, in particular haploid and dihaploid plants. In one embodiment, the plants regenerated from the embryos comprise less than 30% preferably less than 20%, still preferably less than 10%, even more preferably less than 5% haploid plants. In another embodiment, the plants regenerated from the embryos comprise no haploid plants or essentially no haploid plants. In another embodiment, the plants regenerated from the embryos comprise more than 20%, preferably more than 30%, still preferably more than 40% dihaploid plants. In another embodiment, the ratio dihaploid:haploid in the regenerated plants is above 1:1 preferably above 2:1, still preferably above 3:1, even more preferably above 5:1 or 10:1.

Dihaploid plants are particularly useful, as they can be used as such for plant breeding and plant improvement programs. Haploid plants are also useful but require a step of doubling of their chromosome stock to be used for plant breeding and plant improvement.

The present inventors have surprisingly observed that the methods according to the present invention promote a spontaneous doubling of the stock of chromosomes of the microspores and/or embryos in culture, thereby favoring the generation of dihaploid plants over haploid plants. This unexpected result is highly advantageous, as it avoids having to artificially doubling the stock of chromosome of haploid plants through the use of chromosome doubling agents, some of which are hazardous chemical products.

In one embodiment, the methods of the present invention comprise a further step of selecting haploid, diploid or haploid and diploid plants from the regenerated plants. This step can be carried out by analyzing the ploidy of the regenerated plants, for example by flow cytometry. Such analysis enables the classification and sorting of the plants according to their ploidy, for example n (haploid), 2n (diploid), 3n and more (polyploid).

Optionally, the genome of the plants can be further analyzed through the use of one or more molecular markers to sort dihaploid plants (respectively polyhaploid plants) from the rest of diploid plants (respectively polyploid plants). This step enables a distinction between diploid plants derived from a somatic cell and dihaploid plants from a spontaneous doubling of the chromosome stock of a haploid cell (e.g. an isolated microspore). Indeed, dihaploid plants are homozygous or essentially homozygous, whereas diploid plants derived from a somatic tissue will normally comprise heterozygous locuses, in particular if the donor plant is a non-fixed line, for example a hybrid plant. Hence, analysis of the zygosity of a molecular marker which is heterozygous in the donor plant will reveal whether a diploid plant is dihaploid. Preferably, several molecular markers are analyzed to increase the statistical significance of the assay and reduce the risk that a non-homozygous plant appears as homozygous with a particular molecular marker used. In particular, at least 2, preferably at least 3, 4, 5, 6, 7, 8 or 9 molecular markers can be used. Non-limiting examples of molecular markers which can be used for this analysis include, but are not limited to Single Nucleotide Polymorphisms (SNPs) or microsatellite markers (SSR).

It must be noted, in this respect, that the use of isolated microspore cultures, and not anther cultures, reduces considerably the risk of contamination by somatic tissue, and thereby the risk of giving rise to a diploid plant derived from somatic tissue. Hence, in certain embodiments, the step of analyzing the plants through the use of one or more molecular markers can be avoided.

In one embodiment, the methods according to the present invention comprises a step of doubling of the chromosome stock of the regenerated haploid plants, preferably by means of a chromosome doubling agent such as colchicine.

This technique of doubling of the chromosome stock by means of a chromosome doubling agent advantageously comprises the following successive stages:
1. Isolate the main growing tip of the plant as well as axillary buds if there are any;
2. Prepare a solution of colchicine and then sterilize it;
3. Put the cuttings in small sterile Petri dishes;
4. Pour in a sufficient amount of colchicine to cover them, then close the Petri dishes;
5. Leave to soak for several hours;
6. Take out the cuttings and rinse them in pots of sterile water;
7. After drying them a little on sterile paper, transplant all the cuttings onto their original medium;
8. Transplant developing buds on the original medium;
9. When the cuttings have rooted, bring them out in vivo on a substrate comprising a nutrient solution.

The stock of chromosome can also be artificially doubled at the embryo stage. Hence, in one embodiment of the present invention, the method according to the present invention comprises contacting an embryo with a chromosome doubling agent. In preferred embodiments, the chromosome doubling agent is colchicine.

Further examples of chromosome doubling agents include, but are not limited to acetyltrimethylcolchicinic acid derivatives, carbetamide, chlorpropham, propham, pronamide/propyzamide tebutam, chlorthal dimethyl (DCPA), Dicamba/dianat/disugran (dicamba-methyl) (BANVEL, CLARITY), benfluralin/benefin/(BALAN), butralin, chloralin, dinitramine, ethalfluralin (Sonalan), fluchloralin, isopropalin, methalpropalin, nitralin, oryzalin (SURFLAN), pendimethalin, (PROWL), prodiamine, profluralin, trifluralin (TREFLAN, TRIFIC, TRILLIN), AMP (Amiprofos methyl); Butamifos, Dithiopyr and Thiazopyr.

The present description will be further illustrated by the following examples, which should not be construed as limiting in any way.

EXAMPLES

Example 1: Attempts to Obtain Haploid/Dihaploid *Cucumis sativus* Plantlets by Isolated Microspore Culture (IMC)

The present inventors have tried to produce haploid and dihaploid *Cucumis sativus* plantlets according to the protocols described in Zhan et al., *Acta. Horticulturae Sinica*, 2009, 36 (2), 221-226.

Plants of varieties MP5348, TMG1-A, HM81, HM82, HMX4453 and Poinsett 97 are cultivated and buds with microspores at the late-uninucleate stage are collected according to the indications given in Zhan et al. MP5348 is a monoecious open-pollinated Beit Alpha type, TMG1-A is a monoecious open-pollinated Chinese cucumber type, HM81 is a monoecious open-pollinated pickle type, HM82 is a monoecious determine hybrid pickle type, HMX4453 is a monoecious hybrid slicer type and Poinsett 97 is a monoecious open-pollinated slicer type.

The buds are pretreated 2 days in 4° C. The buds are then sterilized, and the microspores are isolated from the bud tissue, according to the indications given in Zhan et al.

The microspores are cultured according to the indications given in Zhan et al. Briefly, the microspores are suspended in a culture medium and the microspore density is adjusted to about $1.0 \times 10^5$ cells/mL. The culture medium is a NLN or B5 basal medium supplemented with 0.5 mg/L 2,4-D and 0.2 mg/L 6-BA. The medium has been filter sterilized using 0.22 pm pore size filter, the concentration of sucrose is 13% and the pH is 5.8.

The isolated microspores in the liquid medium were cultured in. Petri dishes of 60 mm diameter, and cultured in 24 hour dark conditions at 25° C.

After 30 days, the cultures are observed. The microspores have not divided, and no embryos, embryoids or multicellular structures are obtained.

Example 2: Production of Dihaploid *Cucumis sativus* Plantlets

1. Growth of the donor plants

The seeds of different genotypes of *Cucumis sativus* such as HMX4453, PI518848 and Poinsett97 are sown into one inch deep in 24-cell flats: one seed is planted per cell in pre-watered "Sunshine Seedling Soil Mix 1". Poinsett 97 is an American Slicer type. It is an open-pollinated variety which is monoecious. HMX4453 is a proprietary experimental hybrid from HM.Clause Inc. It is an American Slicer type which is predominantly female, but does produce some males. PI518848 is a Chinese long type, genetically distant from the American Slicers, and closer to wild cucumbers. It is monoecious.

Flats are placed on a heating pad set to 28° C. and seeds germinate in about one week. At this point in time, they do no longer require the heating pad. When there are fully expanded true leaves, seedlings are ready for transplant in controlled environment such as a greenhouse.

Seedling Transplant: the seedlings are transplanted 2-4 weeks from planting into 1-3 gallon soil bags or pots containing pre-watered Redi-Gro Planting Mix. The temperature should be 22-26° C. during the day and 12° C.-20° C. at night, with humidity at range 65-80%. Day length should be 12-16 hours with light density at 200-900 µmol $m^{-2} S^{-1}$.

Irrigation and Fertigation: Plants should be watered by a timed drip system (or by hand) daily. As plants grow and increase transpiration rate, the amount of water delivered should be increased to keep soil evenly moist but not saturated. Slow Release fertilizer or liquid soluble fertilizer can be used. Liquid soluble fertilizer should be applied with a pH of 6.7 and electrical conductivity (EC) 1.2-1.9 mS if fertilizing daily. If fertilizing by hand weekly, EC should be 2.2-2.3 mS. Typically, 15-5-15 plus $Ca^{2+}$ and Mg2+ is the preferred soluble fertilizer, but 14-5-38 plus MgSO4 and CaNO3, and 15-0-0+$Ca^{2+}$ can also be used.

Pest and Disease Control: the product Marathon could be applied at the time of seedling transplanting for control of whiteflies and aphids; Azatin could be used as a drench if fungal gnats persist and increase in population; Kaligreen and Actinovate could be used for control of powdery mildew; sulfur burners can aid in control of powdery mildew if plants are not sensitive to scorching, though there is some indication cucumbers are sensitive to sulfur.

Biological controls could also be done via Koppert Biological Systems products: Thripex sachets for thrips, Entomite in soil for thrips and fungal gnats, and/or Spidex biologicals to control 2-spotted spider mites.

Cultivation of the donor plants: Vines are trained vertically and lowest leaves removed to promote air circulation and prevent disease. Plastic clips or twist ties can be used to help support and train the vines. Plants are not routinely pruned in order to maximize bud production, but may be trimmed at the bottom for aeration and spacing issues.

2. Budding and Life Cycle

The budding or bud collection begins about 3-4 weeks from plant emergence. The first week of budding may not produce enough buds to collect for isolation, but the number of buds should increase as the plant grows to maturity. Peak production, and likely the best time for isolations, is about 6-8 weeks from seed sowing (3-5 weeks from seedling transplant.) At about eight weeks the plants begin to decline in bud production. The plants do not produce useful buds much longer after this time and should be discarded when buds appear to be lower in quality. The entire process from sowing seed to discarding plants is approximately 9-10 weeks.

The present inventors have identified advantageous conditions for the bud collection, by showing that a low night temperature of the plant cultivation before the bud collection has a positive impact of the microspore development. This step increases the efficiency of the microspores to produce embryos by about double when compared to situations when it is not performed (Table 1). This cold shock is for example applied for one day to three days before the bud collection. To the inventors' knowledge, this is the first time that a cold treatment is applied on the plants before the bud collection in view of producing dihaploids and/or doubled haploid cucurbits plants, especially *Cucumis sativus* plants by isolated microspore culture.

TABLE 1

Effect of cold shock on the donor plants

| Growing Location Type | Day Temp (° C.) | Night Temp (° C.) | Cold Shock | % Buds w/Embryos |
|---|---|---|---|---|
| Growth Chamber | 23-24 | 18-19 | NONE | 3.1% |
|  |  |  | 8° C. for 24 Hrs | 9.3% |

3. Bud Selection

The male flower buds are collected in the morning from donor plants that correspond to microspores in the mid-to-late uninucleate to binucleate developmental stage. The majority of microspores should be in the late uninucleate stage. The identification of the proper development stage can be done through staining methods using acetocarmine and light microscopy observations.

4. Disinfection and Preparation of the Buds

The *Cucumis sativus* buds containing the microspore at the appropriate development stage are about between 0.3 to 0.6 cm. They are collected and kept in a beaker containing tap water to maintain humidity. They are stored at 4° C. for 0-4 days as a cold pretreatment and are then rinsed with 4° C. 70% Ethanol for 30 seconds and immediately rinsed with 4° C. sterile water 3 times. Surface-sterilization of the buds is accomplished in 4° C. with 1.0-1.4% sodium hypochlorite (20% Clorox Ultra) solution with the addition of 0.01% Tween-20 along with gentle agitation for 10 minutes, after which the hypochlorite solution is removed and the buds rinsed with 4° C. sterile water 5 times.

5. Isolation of Microspores

All isolations are performed under aseptic conditions and can utilize cold vessels and media (4° C.) to reduce oxidative stress. Twenty to fifty sterilized buds are placed in mortar with 5-20 mL of sterile isolation medium, M404, an MS-B5 based media (Murashige, T and F Skoog, 1962. A revised medium for rapid growth and bioassays with tobacco tissue culture. Physiol. Plant 15: 473-497, Gamborg, OL, RA Miller and K Ojima, 1968. Nutrient requirements of suspension cultures of soybean root cells. Exp. Cell Res. 50:151-158) with 90 g/L of Maltose. The buds are gently ground with the pestle until no anthers are visible in the liquid and the solution is then poured through a sterile 100-200 µM Nylon mesh filter in a sterile beaker. The mortar is rinsed with sterile isolation medium and poured through the same 100 µM Nylon mesh filter and this is done up to a total volume of between 30 to 80 mL. This liquid is then poured through a new 65-80 µM Nylon mesh filter in a sterile beaker and the solution is aliquoted for centrifugations, at 500-1500 RPM for 3 minutes at 4-25° C. (i.e. at room temperature or lower, e.g. about 6° C. in a refrigerated centrifuge). The supernatant is removed and the pellet is re-suspend with isolation medium for a new round of centrifugation, again at 500-1500 RPM for 3 minutes at 4-25° C. This is repeated until a solution of microspores is present without particulate debris from the buds, which shall correspond to about 3 washes.

6. Culture of Microspores

The solution of microspore is diluted to a concentration of about 30,000-150,000 cells/mL using a haemocytometer to count the microspore density. This is done in a Microspore Embryogenesis Induction Medium (MEIM), which components are described in Table 7. The solution is aliquoted by 4-6 mL into 60 mm×50 mm petri plates and sealed, for a heat shock of 24-72 hour at 30-33° C. in the dark.

The isolated microspores are then cultured in the dark at 22-28° C. for about four to five weeks until globular embryos can be seen by bare eyes. This is made possible because the inventors have identified suitable conditions for the microspore cultivation. The inventors have surprisingly discovered that the addition of an inhibitor of deacetylase (HDACi), such as suberoylanilide hydroxamic acid (SAHA), together with polyamine plays a key role in switching the microspore developmental phase from the gametophytic to the sporophytic pathway in cucurbit plants. The addition of SAHA (from day 0 of culture) and polyamines (from day 7-10 of culture) into the culture medium leads to large scale multicellular structures that are formed in 5 to 20 days of cultivation, followed by globular embryos, after about 20 to 40 days of culture.

The MEIM medium complemented with polyamine is referred to as a Microspore embryo development medium (MEDM) which components are described in Table 7.

Table 2 shows the results of various conditions of culture. The culture medium has the composition of the MEIM/MEDM as shown in Table 7, with an optional presence of HDACi and/or polyamine, as indicated in Table 2. In isolated microspore cultures without SAHA and polyamine, multicellular microspore formation is rare if not absent (FIG. 1B). In isolated microspore cultures with SAHA but without polyamine, the multicellular microspore formations are more present but are abnormal (FIG. 2H): the cells are not uniform and the multicellular structures are not compact and form a group of loosen cells. These abnormal multicellular structures cannot be further developed into embryos and plants. By contrast, when both the SAHA and the polyamine are present, embryos could be obtained (FIGS. 1A and 2A to 2D). The best results are obtained when the SAHA is added from day 0 of culture, and polyamine is added subsequently, for example from day 7-10 of culture. Normal embryos have also been obtained when the polyamine is added from day 0 of culture. Another HDACi is tested, trichostatin A (TSA), but experiments with TSA tend to show a lower response than for the SAHA.

Further interestingly, the large scale multicellular structures followed by the formation of globular embryos has been seen for all genotypes tested, showing that the method of the present invention producing embryos through isolated microspore culture is not genotype dependent. The percentage of multicellular induction reached is between about 5 to 15% depending on the histone deacetylase inhibitor used. It is obtained through a digital analysis of microscopic images where the Nikon NIS-Elements Ar Software is discriminating between microspores that have not responded to the treatment and multicellular structures. One will note that the Response % is the percentage of formation of multicellular structures, not the analysis or classification of such structures as normal or abnormal. The last column (classification of the multicellular structures) reflects the observation of the multicellular structures according to criteria which defines whether they are normal or abnormal, i.e. uniformity of the cells, and compactness of the multicellular structures.

TABLE 2

Effect of HDACi and polyamine addition

| Cultivar | Example Experiment | HDACi Treatment | Polyamine treatment | Response (% of formation of multicellular structures) | Classification of the multicellular structures |
|---|---|---|---|---|---|
| PI518848 | Control | None | None | 0% | — |
| PI518848 | Treatment 1 | SAHA (5 µM) | None | 13.7% | Abnormal |
| PI518848 | Treatment 2 | SAHA (10 µM) | None | 17.3% | Abnormal |
| PI518848 | Treatment 3 | SAHA (10 µM) | Putrescine (100 ppm) | 16.5% | Normal |
| PI518848 | Treatment 4 | TSA (0.5 µM) | None | 4.3% | Abnormal |
| HMX4453 | Control | None | None | 0.0% | — |
| HMX4453 | Treatment 1 | SAHA (10 µM) | None | 9.6% | Abnormal |
| HMX4453 | Treatment 2 | SAHA (10 µM) | Putrescine (100 ppm) | 9.9% | Normal |

7. Embryo development to torpedo and cotyledonary embryos induced from IMC

Figure 2:
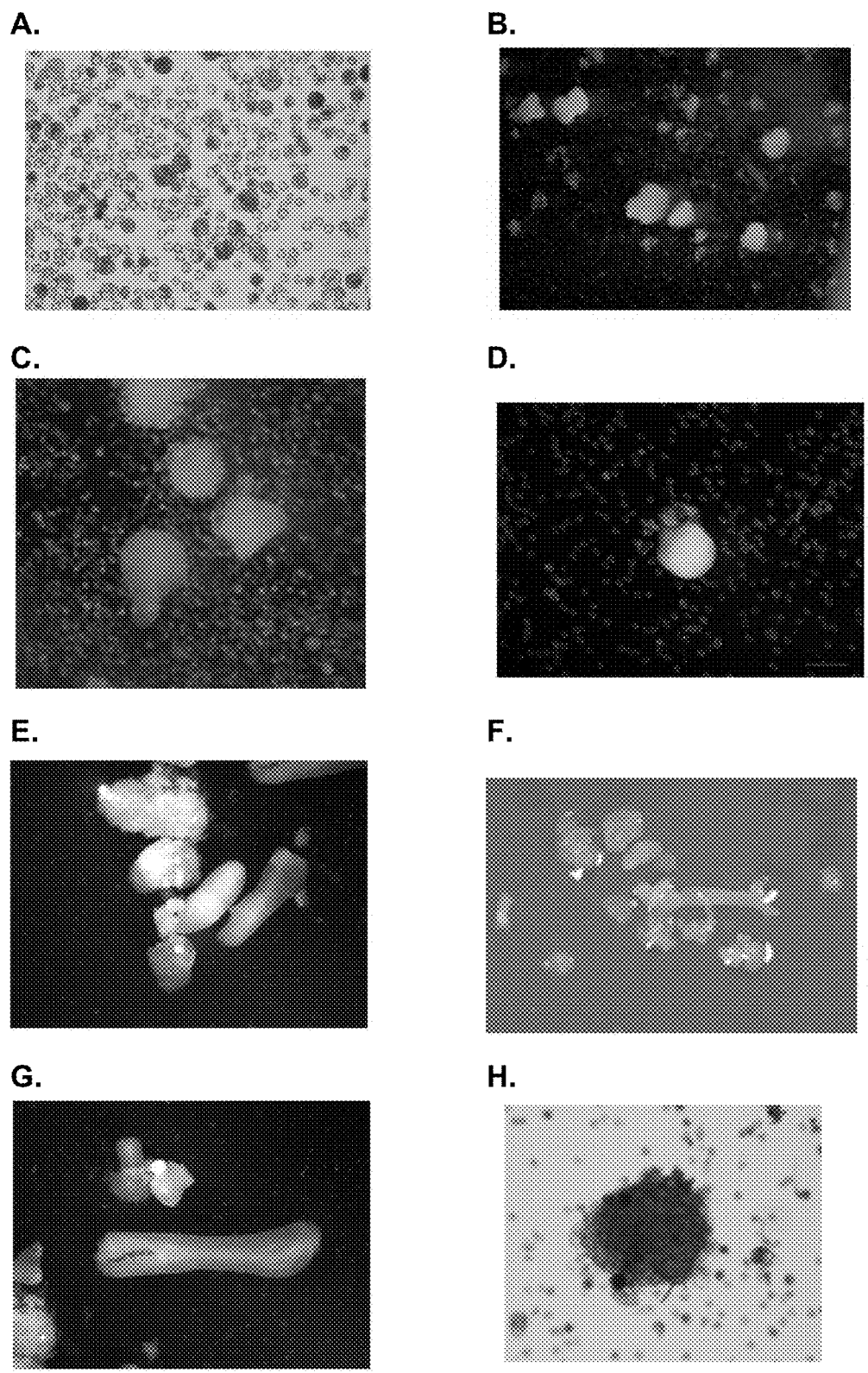
FIG. 2: light micropcy images of microspore and embryo cultures. Panel (A) shows microspore cultures induced by SAHA. Panels (B), (C) and (D) show developed globular embryos in bilayer medium, wherein the embryos have been obtained by culture of isolated microspores with SAHA and polyamines. Panels (E), (F) and (G) show elongated dipolar and cotyledonary embryos. Panel (H) shows an example of abnormal embryo development in a culture medium comprising SAHA without polyamine.

Globular embryos are visible after 20 to 40 days of culture in MEDM medium. To obtain elongated embryos, the inventors have used a bilayer culture system on a rotary shaker at 50-70 rpm in the dark for about 30 day, which has enabled the elongation of the embryos (FIG. 2E to 2G). The bilayer culture system is made of two layers, one lower solid medium made of MEEM with activated charcoal and solidified with 7 g/L agar (see Table 7) and one upper liquid medium, still made of MEDM supplemented with 1-2 ppm abscisic acid and containing the embryos to be elongated.

By contrast, culture of the globular embryos in a Microspore Embryo Elongation Medium (MEEM) alone, is less effective to generate elongated embryos.

8. Plantlet Regeneration

Figure 3:
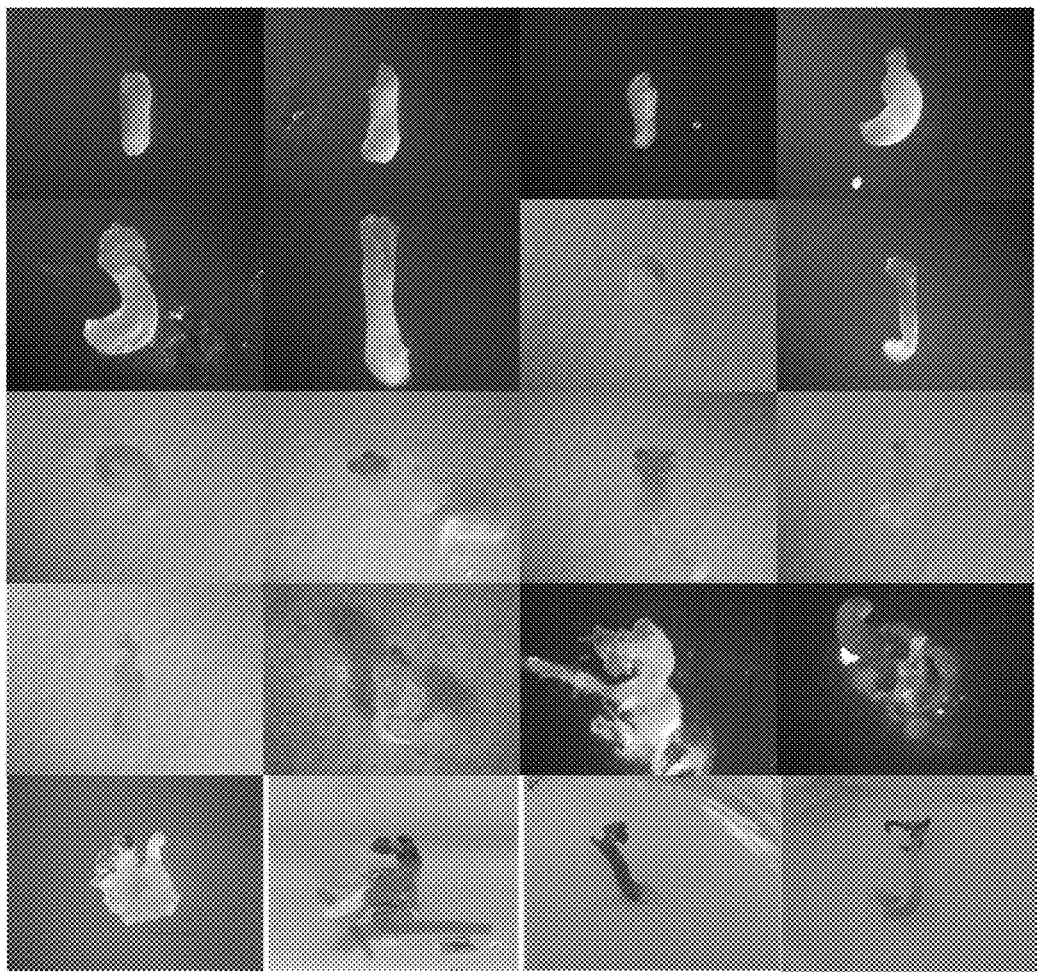
FIG. 3: Regeneration of various microspores derived-elongated torpedo and cotyledonary embryos to normal plantlets in solid medium after removal from bilayer medium. the first row of pictures represent torpedo embryos, the $2^{nd}$ and $3^{rd}$ rows of pictures represent cotyledonary embryos, $4^{th}$ and $5^{th}$ rows of pictures represent continuously developed cotyledonary embryos toward plantlets.

The elongated embryos further develop into cotyledonary embryos that are then subcultured onto solid embryo normalization medium (MENM) until normal plantlets formation, when visible elongation and differentiation of roots and meristem regions are visible (FIG. 3).

Figure 4:
FIG. 4: Panel (A) shows cucumber plantlets regenerated according to the present invention. Panel (B) shows regenerated diploid plants successfully transplanted into greenhouse conditions with normal phenotype. Panel (C) shows flowers from diploid regenerated plants. When tested for pollen germination under light microscopy, ~100% pollen germination is obtained.
Figure 4:
Figure 4:
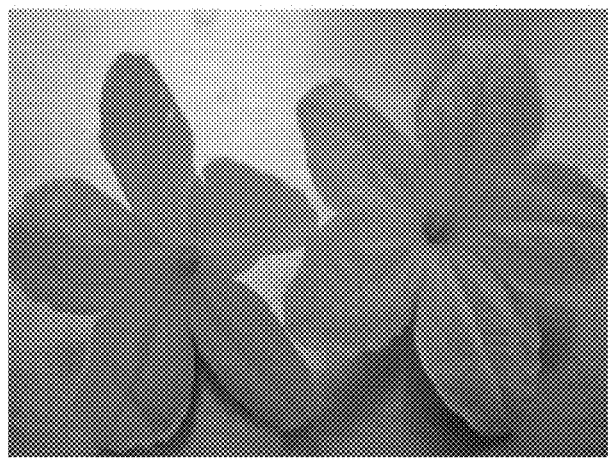

Then, the plantlets are placed into a mist chamber for 3 to 4 days where reduced light and high humidity promotes rooting. They can then be transferred into greenhouses for acclimation steps (FIG. 4).

9. Analysis of the Ploidy of the Plants Obtained through the Process

The plantlets that have reached the 4 to 6 leaf stage of development are checked for their ploidy level by flow cytometry which allows a reliable distinction between 2n and n plants. The ploidy level could be analysed for example according to the protocols developed by Laat et al. in Theo. Appl. Genet, 1984, 67: 463-467 and in Plant Breeding, 1987, 99: 303-307.

Interestingly, no haploid plants have been obtained, while about 50% of the plantlets are diploid (Table 3).

TABLE 3

Level of ploidy of the regenerated plants

| Ploidy | Nb. Regenerated Plants |
|---|---|
| 2n | 17 |
| 3n | 2 |
| 4n | 19 |
| Aneuploid/Alloploid | 2 |
| Total | 40 |

As the original material worked with is isolated microspores from anthers, i.e. cell with n chromosomes, this result might have two explanations: in the first case, the regenerated plantlets have not been produced from the microspores but rather from some anther cells and in such a case, while they are 2n plants they shall have the same genotype as the original plant from which the buds were collected. In the second case, this would tend to show that the plantlets are dihaploid plants, i.e. plants in which the original cell was haploid and whose chromosome stock has doubled spontaneously. This will be solved by the last step of the process, namely the use of molecular markers as described hereafter.

It must be noted that if one had obtained haploid plants, such haploid plants could have been submitted to chemical treatments such as colchicine, leading to an artificial doubling of the chromosome stock, i.e. doubled haploid plants. The man skilled in the art knows how to perform such chromosomal stock doubling through colchicine.

10. Analysis of the DNA

This step is the final confirmation of the dihaploid nature of the regenerated plants. Indeed, for a given locus, the original plant which is a non-fixed line, such as a hybrid, has two different alleles, such as X and Y.

If the regenerated 2n plants have been produced from any 2n plant cell from the original plant, it shall continue to contain both alleles at any given locus. If, on the contrary the plants have been produced as expected through the isolated microspore culture method of the invention, then they shall carry only one allele at a given locus, in two copies.

A sample is taken from each plant, and the DNA is extracted using the ArchivePure DNA Isolation Kit by 5 Prime (www.5prime.com). The PCR reaction is performed in a reaction volume of 5 µL consisting of 2.5 µL of diluted DNA and a 2.5 µL mixture of proprietary KASPAR PCR reaction mix by LGC Genomics and SNP assay. The KASPAR reaction mix consists of 2.5 µl of KASPAR PCR reagent and 0.07 µl of SNP assay mixture per sample reaction.

The PCR reaction consists of several cycles of amplification, described as follows: 94° C. for 15 minutes, a 2 step 10 cycle Touchdown cycle of 94° C. for 20 seconds followed by 65° C. for 1 minute with each cycle's Tm decreasing by −0.8° C. The final amplification cycle consists of 35 cycles of 94° C. for 20 seconds and 57° C. for 1 minute.

TABLE 4

SNP analysis of the diploid plants

|  | SNP1 | SNP2 | SNP3 | SNP4 | SNP5 | SNP6 | SNP7 |
|---|---|---|---|---|---|---|---|
| Donors | X:Y | X:Y | X:Y | X:Y | X:Y | X:Y | X:Y |
| DH1 | X:X | Y:Y | X:X | Y:Y | Y:Y | X:X | Y:Y |
| DH2 | X:X | Y:Y | X:X | Y:Y | Y:Y | Y:Y | Y:Y |
| DH3 | Y:Y | Y:Y | Y:Y | Y:Y | Y:Y | Y:Y | X:X |
| DH4 | Y:Y | Y:Y | X:X | Y:Y | Y:Y | X:X | X:X |
| DH5 | X:X | Y:Y | Y:Y | Y:Y | Y:Y | X:X | X:X |
| DH6 | X:X | Y:Y | X:X | Y:Y | Y:Y | Y:Y | Y:Y |
| DH7 | X:X | Y:Y | Y:Y | Y:Y | Y:Y | X:X | Y:Y |

For each plant tested and for each of the SNP tested, the results clearly show that the regenerated diploid plants are dihaploid plants (Table 4).

Example 3

Heat Shock on the Isolated Microspores

Isolated microspores were obtained according to the method described in Example 2, and cultured. Table 5 shows the effect of a heat shock on the IMC, prior to the culture of the isolated microspores, using the PI518848 line. A heat shock of 1-3 days at 30° C., applied to the isolated microspores prior to their culture, improves the rate of embryo production.

TABLE 5

Test of different heat shock conditions

| Culture Conditions | Nb. Experiments | Avg. exp. Response to multicellular % | Embryo Production Rate/exp. |
|---|---|---|---|
| No heat shock, culture at 25° C. | 78 | 0.72% | 5.24 |
| Heat shock (30° C., 1 day), culture at 25° C. | 168 | 1.40% | 6.27 |
| Heat shock (30° C., 2 days) culture at 25° C. | 14 | 0.71% | 6.00 |
| Heat shock (30° C., 3 days) culture at 25° C. | 15 | 4.20% | 7.53 |

"Avg.exp.response to multicellular %" respresents the percentage of cultures yielding multicellular structures, calculated over total experiments from all age of donor materials, including non-response experiments.
"Embryo Production Rate/exp" respresents the ratio of embryos obtained to the number of experiments where multicellular structures have been obtained.

Example 4

Tests of Various Compounds within the Isolated Microspore Culture Media

Isolated microspores are obtained according to the method described in Example 2, and cultured. Table 6 shows the observation results at first 4 weeks of culture (i.e. prior to embryo elongation in a bilayer culture), using different culture media. All media comprise M404 basal medium and carbohydrates as in the MEIM composition described in Table 7, supplemented with 10 µM SAHA plus various other additional compounds. "Event" represents embryogenic callus or embryos.

The microspore cultures are evaluated for their production of multicellular structures and/or normal embryos. As shown in Table 6 below, polyamines (putrescine in this particular case) are the sole compounds which, in association with SAHA, enable the development of normal embryos from the isolated microspores.

TABLE 6

Test of various compounds within the IMC media

| In all media: SAHA (10 µM) | Multicellular structures | Normal embryos |
|---|---|---|
| 2,4-D (0.5 ppm) + BA (0.2 ppm) | | |
| No Additional | x | — |
| Activated Charcoal (0.02%) | x | — |
| Activated Charcoal (0.2%) | — | — |
| Adenine-Sulphate (ADE-S) (20 ppm) | — | — |
| ADE-S (20 ppm) + AC (0.02%) | x | — |
| ADE-S (20 ppm) + AC (0.2%) | — | — |
| AgN03 (1 ppm) | — | — |
| BR (0.02 ppm) | x | — |
| BSO (0.1 mM) | — | — |
| BSO (0.5 mM) | — | — |
| Putrescine (100 ppm) | x | x |
| Triacontanol (2 ppm) | — | — |
| Triacontanol (4 ppm) | — | — |
| Jasmonic Acid (1 ppm/24 h) | — | — |
| Colchicine (500 µM/24 h) | — | — |
| Colchicine (25 µM/24 or 48 h) | — | — |
| 2,4-D (0.5 ppm) + ZeaR (2 ppm) | | |
| No Additional | x | — |
| 2,4-D (0.5 ppm) + ZeaR (2 ppm) | | |
| No Additional | x | — |
| No Auxin + No Cytokinin | | |
| No Additional | x | — |

TABLE 6-continued

Test of various compounds within the IMC media

| In all media: SAHA (10 μM) | Multicellular structures | Normal embryos |
|---|---|---|
| No Auxin + ZeaR (4 ppm) | | |
| No Additional | x | — |

"x" means that multicellular structures or normal embryos have been obtained.
"—" means that multicellular structures or normal embryos have not been obtained.
AC: Activated charcoal
BR: brassinoids
BSO: buthionine-sulfoximine (gluthathione biosynthesis inhibitor acting by inhibiting γ-glutamylcysteine synthetase).
ZeaR: trans-zeatin-riboside
24/48 h means that the subject compound is included in the culture media at day 0 of culture, and washed out after 24 hours/48 hours of culture.

Example 5

Description of the Culture Media

Exemplary compositions of the culture media used in the present experiments are given hereafter.

TABLE 7

Media composition

| Component (mg/L, unless otherwise specified) | MEIM | MEDM | MEEM | MENM |
|---|---|---|---|---|
| M404 | full | full | Full | Half-full |
| Carbohydrates | 30,000-170,000 | 30,000-170,000 | 30,000-120,000 | 30,000-120,000 |
| Agar | 0 | 0 | 7,000 | 7,000 |
| HDACi | 0.5-40 μM SAHA or 0.001-1.0 μM TSA | 0.5-40 μM SAHA or 0.001-1.0 μM TSA | 0 | 0 |
| Polyamine | 0 | 5-200 | 5-200 | 0 |
| BA | 0.05-2 | 0.05-2 | 0.05-2 | 0.05-2 |
| 2,4-D | 0.05-2 | 0.05-2 | 0.05-2 | 0 |
| PAA | 0.5-50 | 0.5-50 | 0 | 0 |
| Activated charcoal | 10-100 | 10-100 | 1,000-5,000 | |

MEIM: Microspore embryogenesis induction medium (MEIM).
MEDM: Microspore embryo development medium (MEDM).
MEEM: Microspore embryo elongation medium (MEEM).
MENM: Microspore embryo normalization medium (MENM).
Polyamine: putrescine, spermine and/or spermidine. (e.g. 100 ppm of putrescine). A polyamine mixture can be used, e.g. putrescine, spermine, spermidine (exemplary ratios: spermine:putrescine = 1:1 to 1:100; spermidine:putrescine = 1:1 to 1:100).
M404: Murashige & Skoog (MS) basal medium w/Gamborg vitamins, PhytoTechnology Laboratories ®USA.
PAA: phenylacetic acid
Carbohydrates: Maltose, Sucrose.

Example 6

Additional Production of Dihaploid *Cucumis Sativus*

In addition to the genotypes mentioned in Example 2, the present inventors have further performed the method of the invention on 7 further different genotypes of *Cucumis sativus* namely A196, CXP 1136, TMG-1, Poinsett 76, Poinsett 88, PI 267197 and Poinsett 97.

A196 is a proprietary experimental hybrid from HM.Clause Inc. It is a semi-multi, gynoecious and parthenocarpic beit alpha for greenhouse production.

CXP 1136 is a proprietary experimental hybrid from HM.Clause Inc. It is a gynoecious open field beit-alpha type.

TMG-1 is an open-pollinated monoecious accession, of the Chinese Long type.

PI 267197 is an accession collected in China in 1959, available from USDA, it is a Chinese Long type with light skin.

Poinsett 97, as previously mentioned, is an open pollinated monoecious variety of the American Slicer type.

Poinsett 76 and Poinsett 88 also are open pollinated, monoecious American Slicer varieties.

All experimental conditions are similar to the ones described in Example 2.

As shown in Table 8 below, for all tested genotypes, the combination of a HDACi treatment and a polyamine treatment enables the development of normal multicellular structures forming a compact group of uniform cells, which can be further developed into embryos and plants.

These results can be compared with the control conditions of Example 2, showing that microspores cultured without HDACi and polyamine do not develop into multicellular structures (0% of formation of multicellular structures), and further showing that an HDACi treatment without polyamine results in the formation of abnormal multicellular structures which cannot be developed into embryos and plants. The abnormal multicellular structures which develop without polyamine in the culture medium are not compact and form a group of loosen cells which lack uniformity.

TABLE 8

Effect of HDACi and polyamine addition on other Cucumber genotypes

| Cultivar | Example Experiment | HDACi Treatment | Polyamine Treatment | Response (% of formation of multicellular structures) | Classification of the multicellular structures |
|---|---|---|---|---|---|
| A196 | Treatment | SAHA (10 μM) | Putrescine (100 ppm) | 8.71% | Normal |
| CXP 1136 | Treatment | SAHA (10 μM) | Putrescine (100 ppm) | 8.01% | Normal |
| TMG-1 | Treatment | SAHA (10 μM) | Putrescine (100 ppm) | 2.50% | Normal |
| Poinsett 76 | Treatment | SAHA (10 μM) | Putrescine (100 ppm) | 2.25% | Normal |
| Pointsett 88 | Treatment | SAHA (10 μM) | Putrescine (100 ppm) | 1.35% | Normal |
| PI 267197 (chinese long) | Treatment | SAHA (10 μM) | Putrescine (100 ppm) | 1.32% | Normal |
| Pointsett 97 | Treatment | SAHA (10 μM) | Putrescine (100 ppm) | 1.16% | Normal |

This example confirms that the method of the invention is non-genotype dependent and allows the provision of normal multicellular structures which can be developed into haploid, dihaploid, polyhaploid and/or doubled haploid embryos and plants, irrespectively of the genotype of the *Cucumis sativus* microspores used as starting material.

Example 7

Production of Dihaploid *Cucumis Melo*

In addition to the *Cucumis sativus* genotypes mentioned in Example 2 and in Example 6, the present inventors have performed the method of the invention on 7 different genotypes of *Cucumis melo* namely Gaudio, Anasta, Gandalf, Calico, Deluxe, HMX 5590 and Magenta.

Gaudio is an Italian Netted melon type, monoecious F1 hybrid, available from HM. Clause.

Anasta is a Netted charentais melon type, monoecious F1 hybrid, available from HM. Clause.

Gandalf is a Netted charentais melon type, monoecious F1 hybrid, available from Nunhems.

Calico is an Italian Netted melon type, monoecious F1 hybrid, available from HM. Clause Deluxe is an HM.Clause hybrid western shipper variety, orange fleshed and fully netted, well adapted to the southwestern U.S.

HMX 5590 is an HM.Clause hybrid long shelf life Harper type. It is fully netted, orange fleshed and will be adapted to growing regions in Central America and California.

Magenta is a Netted charentais Long Shelf-life melon type, monoecious F1 hybrid, available from Nunhems.

All experimental conditions are similar to the ones described in Example 2.

As shown in Table 9 below, for all tested genotypes, the combination of a HDACi treatment and a polyamine treatment enables the development of normal multicellular structures forming a compact group of uniform cells, which can be further developed into embryos and plants.

These results can be compared with the control conditions of Example 2, showing that microspores cultured without HDACi and polyamine do not develop into multicellular structures (0% of formation of multicellular structures), and further showing that an HDACi treatment without polyamine results in the formation of abnormal multicellular structures which cannot be developed into embryos and plants. The abnormal multicellular structures which develop without polyamine in the culture medium are not compact and form a group of loosen cells which lack uniformity.

TABLE 9

Effect of HDACi and polyamine addition on various melon genotypes

| Cultivar | Example Experiment | HDACi Treatment | Polyamine Treatment | Response (% of formation of multicelluer structures) | Classification of the multicellular structures |
|---|---|---|---|---|---|
| Guadio | Treatment | SAHA (10 μM) | Putrescine (100 ppm) | 3.31% | Normal |
| Anasta | Treatment | SAHA (10 μM) | Putrescine (100 ppm) | 2.24% | Normal |
| Gandalf | Treatment | SAHA (10 μM) | Putrescine (100 ppm) | 2.21% | Normal |
| Calico | Treatment | SAHA (10 μM) | Putrescine (100 ppm) | 2.17% | Normal |
| Deluxe | Treatment | SAHA (10 μM) | Putrescine (100 ppm) | 0.89% | Normal |
| HMX5590 | Treatment | SAHA (10 μM) | Putrescine (100 ppm) | 0.77% | Normal |
| Magenta | Treatment | SAHA (10 μM) | Putrescine (100 ppm) | 0.54% | Normal |

This example confirms that the method of the invention is non-genotype dependent and non-species dependent amongst the Cucurbitaceae family. The method of the invention thus allows the provision of normal multicellular structures which can be developed into haploid, dihaploid, polyhaploid and/or doubled haploid embryos and plants, irrespectively of the species and genotype of the cucurbits microspores used as starting material.

Although the invention has been described and illustrated in the foregoing illustrative embodiments it is understood that the present disclosure has been made only by way of example, and that numerous changes in the details of implementation of the invention can be made without departing from the spirit and scope of the invention, which is only limited by the claims which follow. In particular, features of the disclosed embodiments can be omitted, combined and rearranged in various ways.

The invention claimed is:

1. A method for producing haploid, dihaploid, polyhaploid and/or doubled haploid plants of the family Cucurbitaceae from isolated microspores, wherein said method comprises:
   a) culturing isolated microspores to obtain embryos competent for plant regeneration, wherein the microspores have been isolated from plant material of a donor plant of the family Cucurbitaceae; and
   b) regenerating plants from the embryos;
   wherein step (a) comprises contacting the microspores with one or more inhibitor of histone deacetylase (HDACi) and one or more aliphatic polyamine.

2. The method of claim 1, wherein step (a) comprises inducing the sporophytic development of the microspores in a culture medium comprising the HDACi and subsequently adding the polyamine in the culture of isolated microspores.

3. The method of claim 2, wherein the polyamine is added no sooner than the isolated microspores have divided in culture.

4. The method of claim 1, wherein the HDACi is selected from hydroxamic acids, cyclic tetrapeptides, depsipeptides, aliphatic acids, benzamides, electrophilic ketones, and mixtures thereof.

5. The method of claim 4, wherein the HDACi is selected from suberoylanilide hydroxamic acid (SAHA), trichostatin A (TSA) and mixtures thereof.

6. The method of claim 1, wherein the polyamine is selected from putrescine, spermidine, spermine, and mixtures thereof.

7. The method of claim 1, wherein said step (a) comprises:
   (i) culturing the isolated microspores to obtain globular embryos; and
   (ii) culturing the globular embryos to obtain elongated embryos;
   wherein step (ii) comprises at least one of:
   culturing the globular embryos in the presence of an adsorbent material;
   culturing the globular embryos in a multilayer culture system, comprising a liquid phase overlaying a solid phase;
   culturing the globular embryos under agitation; and
   culturing the globular embryos in the dark.

8. The method of claim 7 wherein the solid phase comprises activated charcoal and/or the liquid phase comprises at least one of abscisic acid and one or more polyamine.

9. The method of claim 1, wherein the plant material of the donor plant has been obtained through the steps of:
   growing a donor plants of the family Cucurbitaceae;
   subjecting the donor plant to a stress treatment; and
   recovering plant material containing microspores at a developmental stage competent for induction of embryo development.

10. The method of claim 1, wherein the microspores have been isolated from the plant material of the donor plant at a mid-uninucleate to early binucleate stage of development.

11. The method of claim 1, wherein the isolated microspores have been subjected to a stress treatment, prior to step (a).

12. The method of claim 1, wherein the donor plant belongs to the genera *Cucumis, Cucurbita* or *Citrullus*.

13. The method of claim 1, wherein the donor plant is parthenocarpic, and/or wherein the donor plant is selected from a monoecious, dioecious, gynoecious, androecious, andromonoecious, gynomonoecious, hermaphrodite, protoandrous or protogynous plant.

14. The method of claim 1, further comprising a step of doubling of the chromosome stocks of the haploid plants regenerated at step (b).

15. A method for producing haploid, dihaploid, polyploid and/or doubled haploid embryos of the family Cucurbitaceae from isolated microspores, wherein said method comprises:
   a) culturing isolated microspores to obtain embryos, wherein the microspores have been isolated from plant material of a donor plant of the family Cucurbitaceae,
   wherein step (a) comprises contacting the microspores with one or more inhibitor of histone deacetylase (HDACi) and one or more aliphatic polyamine.

16. The method of claim 1, further comprising the step of crossing a plant regenerated at step (b), with another plant of the family Cucurbitaceae and obtaining seeds and/or progeny plants.

* * * * *